United States Patent
Kuo et al.

(10) Patent No.: US 9,321,762 B2
(45) Date of Patent: Apr. 26, 2016

(54) QUINAZOLINE COMPOUNDS, METHOD FOR PREPARING THE SAME AND USE THEREOF

(71) Applicant: DEVELOPMENT CENTER FOR BIOTECHNOLOGY, New Taipei (TW)

(72) Inventors: Mann-Yan Kuo, New Taipei (TW); Chu-Bin Liao, New Taipei (TW); Shao-Zheng Peng, New Taipei (TW); Shih-Chieh Yen, New Taipei (TW); Nan-Horng Lin, New Taipei (TW)

(73) Assignee: Development Center for Biotechnology, New Taipei (TW)

( * ) Notice: Subject to any disclaimer, the term of this patent is extended or adjusted under 35 U.S.C. 154(b) by 0 days.

(21) Appl. No.: 14/103,662

(22) Filed: Dec. 11, 2013

(65) Prior Publication Data

US 2015/0158854 A1    Jun. 11, 2015

(51) Int. Cl.
| | |
|---|---|
| C07D 417/14 | (2006.01) |
| C07D 239/94 | (2006.01) |
| C07D 401/04 | (2006.01) |
| C07D 403/04 | (2006.01) |

(52) U.S. Cl.
CPC ............ C07D 417/14 (2013.01); C07D 239/94 (2013.01); C07D 401/04 (2013.01); C07D 403/04 (2013.01)

(58) Field of Classification Search
CPC ... C07D 417/14; C07D 401/04; C07D 403/04
USPC ....................... 514/266.2; 544/287
See application file for complete search history.

(56) References Cited

U.S. PATENT DOCUMENTS

2013/0165458 A1    6/2013   Huang et al.

FOREIGN PATENT DOCUMENTS

CN   102558159 A   7/2012

OTHER PUBLICATIONS

McMahon et al. (2000).*
Pinedo et al. (2000).*

* cited by examiner

*Primary Examiner* — Paul V Ward
(74) *Attorney, Agent, or Firm* — Osha Liang LLP

(57) ABSTRACT

A compound for treating a protein kinase-related disease or disorder having a structure of formula (I)

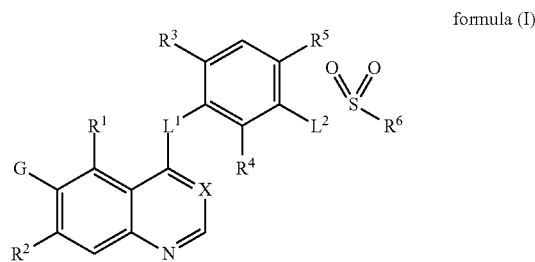

formula (I)

wherein G is a heteroaryl, heterocyclic or alkyne; X is N or CH; $L^1$ is —N($R^7$)—, —O—, —C(S)—, —C(O)—, or —S—; $L^2$ is —N($R^8$)— or —O—; $R^1$ and $R^2$ are independently hydrogen, halogen, hydroxyl, amino, cyano, nitro, carboxy, $C_1$-$C_4$ alkoxy, $C_1$-$C_4$ alkoxy $C_1$-$C_4$ alkoxy, N,N—($C_1$-$C_4$ dialkyl)amino $C_1$-$C_4$ alkoxy, N—($C_1$-$C_4$ alkyl)amino $C_1$-$C_4$ alkoxy, $C_1$-$C_4$ alkanoyl, $C_1$-$C_4$ alkanoyloxy, N—($C_1$-$C_4$ alkyl)amino, N,N—($C_1$-$C_4$ dialkyl)amino, $C_1$-$C_4$ alkanoyl amino, or heterocyclyl, wherein $C_1$-$C_4$ alkyl is optionally substituted with one or more substituents selected from fluorine and chlorine; $R^3$, $R^4$ and $R^5$ are independently hydrogen, fluorine or chlorine; $R^6$ is $C_1$-$C_4$ alkyl or aryl, which is optionally substituted with one or more substituents selected from halogen, hydroxyl, amino, cyano, nitro; or $R^6$ and $R^8$ form a 5-6 membered cyclyl or heterocyclyl.

9 Claims, No Drawings

QUINAZOLINE COMPOUNDS, METHOD FOR PREPARING THE SAME AND USE THEREOF

BACKGROUND OF INVENTION

1. Field of the Invention

The present invention relates to novel chemical compounds and methods for their use in therapy and preparation. In particular, the invention relates to certain substituted quinazoline compounds and to the use for the inhibition, regulation and/or modulation in particular kinase and its related signal transduction.

2. Background Art

Protein kinases (PKs) play important roles in cellular signal pathways that regulate various cell functions such as differentiation, proliferation, migration, survival and apoptosis. These enzymes catalyze the transfer of a phosphate group from ATP to a tyrosine, serine or threonine residue on a protein substrate. The phosphorylation by kinase and dephosphorylation by phosphatase are involved in countless cellular processes that respond to diverse intracellular signals, regulation of cellular functions, and activation or deactivation of cellular operations.

Abnormal PK activity has been linked to cancer as well as metabolic, immunological, and nervous system disorders. Therefore, protein kinases are attractive therapeutic targets for human disease interventions. PK inhibitors, i.e., compounds that block the activities of PKs, have been developed and used widely for clinical applications. While more than thirty PK inhibitors have been approved for use in disease treatments, such as cancer therapy, there is still a need for new PK inhibitors to treat various disorders or to overcome drug-resistance. The identification of effective small molecule compounds that can specifically inhibit signal transduction and cellular proliferation, by modulating PK activity to regulate and modulate inappropriate cell proliferation, differentiation, or metabolism that is essential for processes leading to cancer, would be beneficial.

SUMMARY OF INVENTION

Embodiments of the invention are based on the unexpected finding that certain quinazoline compounds can inhibit activities of protein kinase (e.g., B-Raf, B-Raf(V600E), C-Raf). These properties allow these quinazoline compounds to be used in treating protein kinase-related diseases including cancers.

In one aspect, embodiments of the invention related to quinazoline compounds of formula (I)

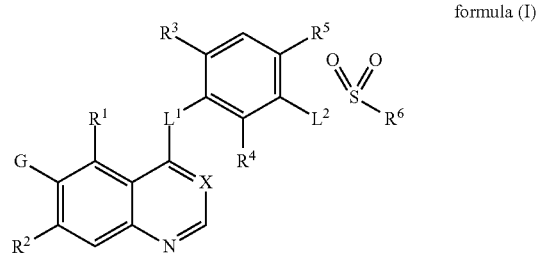

formula (I)

wherein G is a heteroaryl, heterocyclic or alkyne; X is N or CH; $L^1$ is selected from the group consisting of —N($R^7$)—, —O—, —C(S)—, —C(O)—, and —S—; $L^2$ is selected from the group consisting of —N($R^8$)— and —O—; $R^1$ and $R^2$ are independently selected from the group consisting of hydrogen, halogen, hydroxyl, amino, cyano, nitro, carboxy, alkoxy, alkoxyalkoxy, N,N-(dialkyl)aminoalkoxy, N-alkyl amino alkoxy, alkanoyl, alkanoyloxy, N-(alkyl)amino, N,N-(dialkyl)amino, alkanoyl amino, heterocycloalkyl, and heteroalkenyl, wherein the alkyl portion is optionally substituted with one or more substituents selected from fluorine and chlorine; $R^3$, $R^4$ and $R^5$ are independently selected from the group consisting of hydrogen, fluorine and chlorine; $R^6$ is selected from alkyl, alkenyl, alkynyl, and aryl, wherein alkyl, alkenyl, alkynyl, and aryl are optionally substituted with one or more substituents selected from halogen, hydroxyl, amino, cyano, and nitro; alternatively, when $L^2$ is —N($R^7$)—, $R^6$ and $R^8$, together with the atoms to which they are attached, form a 5-6 membered cycloalkyl, cycloalkenyl, or heterocycloalkyl; $R^7$ and $R^8$ are independently selected from hydrogen, alkyl, and alkenyl.

A preferred embodiment of the present invention relates to a compound selected from the group consisting of N-(2,4-difluoro-3-(6-(2-fluoropyridin-3-yl)quinazolin-4-ylamino) phenyl)propane-1-sulfonamide; N-(2,4-difluoro-3-(6-(6-morpholinopyridin-3-yl)quinazolin-4-ylamino)phenyl) propane-1-sulfonamide; N-(2,4-difluoro-3-(6-(6-fluoropyridin-3-yl quinazolin-4-ylamino)phenyl)propane-1-sulfonamide; N-(3-(6-(1H-pyrazol-4-yl)quinazolin-4-ylamino)-2,4-difluorophenyl)propane-1-sulfonamide; N-(2,4-difluoro-3-(6-(pyridin-3-yl)quinazolin-4-ylamino)phenyl) propane-1-sulfonamide; N-(4-fluoro-3-(6-(2-fluoropyridin-3-yl)quinazolin-4-ylamino)phenyl)propane-1-sulfonamide; N-(2,4-difluoro-3-(7-fluoro-6-(2-fluoropyridin-3-yl) quinazolin-4-ylamino)phenyl)propane-1-sulfonamide; N-(2-chloro-4-fluoro-3-(6-(2-fluoropyridin-3-yl)quinazolin-4-ylamino)phenyl)propane-t-sulfonamide; N-(2,4-difluoro-3-(6-(2-fluoropyridin-3-yl)quinazolin-4-ylamino)phenyl)methanesulfonamide; N-(2,4-difluoro-5-(6-(2-fluoropyridin-3-yl)quinazolin-4-ylamino)phenyl)propane-1-sulfonamide; N-(2,4-difluoro-3-(6-(pyridin-4-yl)quinazolin-4-ylamino)phenyl)propane-1-sulfonamide; N-(2,4-difluoro-3-(6-(2-fluoropyridin-3-yl)quinolin-4-ylamino) phenyl)propane-1-sulfonamide; N-(2,4-difluoro-3-(6-(pyridin-4-yl)quinolin-4-ylamino)phenyl)propane-1-sulfonamide; N-(2,4-difluoro-3-(7-fluoro-6-(pyridin-4-yl) quinazolin-4-ylamino)phenyl)propane-1-sulfonamide; N-(2,6-difluoro-3-(6-(2-fluoropyridin-3-yl)quinazolin-4-ylamino)phenyl)propane-1-sulfonamide; N-(2,6-difluoro-3-(6-(pyridin-4-yl)quinazolin-4-ylamino)phenyl)propane-1-sulfonamide; N-(2,4-difluoro-3-(6-(2-fluoropyridin-3-yl) quinazolin-4-ylamino)phenyl)butane-1-sulfonamide; N-(2,4-difluoro-3-(6-(2-fluoropyridin-3-yl)quinazolin-4-ylamino)phenyl)ethanesulfonamide; N-(2,4-difluoro-3-(6-(2-fluoropyridin-3-yl)quinazolin-4-ylamino)phenyl) propane-2-sulfonamide; N-(2,4-difluoro-3-(6-(2-fluoropyridin-3-yl)quinazolin-4-ylamino)phenyl) benzenesulfonamide; N-(3-(7-(2-(dimethylamino) ethylamino)-6-(pyridin-4-yl)quinazolin-4-ylamino)-2,6-difluorophenyl)propane-1-sulfonamide; N-(2,4-difluoro-3-(6-(2-methoxypyridin-3-yl)quinolin-4-ylamino)phenyl) propane-1-sulfonamide; N-(2,4-difluoro-3-(6(2-fluoropyridin-4yl)quinazolin-4-ylamino)phenyl)propane-1-sulfonamide; N-(2,4-difluoro-3-(6-(2-fluoropyridin-4-yl) quinolin-4-ylamino)phenyl)propane-1-sulfonamide; N-(2,4-difluoro-3-(6-(2-oxo-1,2-dihydropyridin-3-yl)quinazolin-4-ylamino)phenyl)propane-1-sulfonamide; N-(2,4-difluoro-3-(6-(6-methoxypyridin-3-yl)quinolin-4-ylamino)phenyl) propane-1-sulfonamide; N-(2,4-difluoro-3-(6-(2-fluoropyridin-3-yl)-7-methoxyquinazolin-4-ylamino)

phenyl)benzenesulfonamide; N-(2,4-difluoro-3-(6-(2-fluoropyridin-3-yl)-7-(2-methoxyethoxy)quinazolin-4-ylamino)phenyl)propane-1-sulfonamide; N-(2,4-difluoro-3-(7-methoxy-6-(pyridin-4-yl)quinazolin-4-ylamino)phenyl) propane-1-sulfonamide; N-(2,4-difluoro-3-(6-(2-methoxypyridin-4-yl)quinazolin-4-ylamino)phenyl)propane-1-sulfonamide; N-(2,4-difluoro-3-(6-(6-oxo-1,6-dihydropyridin-3-yl) quinazolin-4-ylamino)phenyl)propane-1-sulfonamide; N-(2,4-difluoro-3-(6-(6-(2-methoxyethoxy)pyridine-3-yl) quinazolin-4-ylamino)phenyl)propane-1-sulfonamide; N-(2,4-difluoro-3-(6-(2-fluoropyridin-3-yl)quinazolin-4-yloxy) phenyl)propane-1-sulfonamide; N-(3-(6-(6(2-(dimethylamino)ethoxy)pyridin-3-yl)quinazolin-4-ylamino)-2,4-difluorophenyl)propane-1-sulfonamide; N-(2,4-difluoro-3-(6-(6-fluoropyridin-2-yl)quinazolin-4-ylamino)phenyl)propane-1-sulfonamide; N-(2,4-difluoro-3-(6-(6-methoxypyridin-2-yl)quinazolin-4-ylamino)phenyl) propane-1-sulfonamide; N-(2,4-difluoro-3-(6-(6-(2-methoxyethoxyl)pyridin-2-yl)quinazolin-4-ylamino) phenyl)propane-1-sulfonamide; N-(3-(6-(6-(2-(dimethylamino)ethoxy)pyridin-2-yl)quinazolin-4-ylamino)-2,4-difluorophenyl)propane-1-sulfonamide; N-(2,4-difluoro-3-(6-(2-fluoropyridin-3-yl)quinazolin-4-ylamino)phenyl)propane-1-sulfonate; N-(2,4-difluoro-3-(6-(6-morpholinopyridin-2-yl)quinazolin-4-ylamino)phenyl) propane-1-sulfonamide; N-(2,4-difluoro-3-(6-morpholinoquinazolin-4-ylamino)phenyl)propane-1-sulfonamide; N-(3-(6-(1H-imidazol-1-yl)quinazolin-4-ylamino)-2,4-difluorophenyl)propane-1-sulfonamide; N-(2,4-difluoro-3-(6-(2-fluoropyridin-3-yl)quinazolin-4-ylamino)phenyl)-3-fluoropropane-1-sulfonamide; N-(3-(6-(2-(2-(dimethylamino)ethoxy)pyridin-4-yl)quinazolin-4-ylamino)-2,4-difluorophenyl)propane-1-sulfonamide; N-(2,4-difluoro-3-(6-(5-fluoropyridin-3-yl)quinazolin-4-ylamino)phenyl)propane-1-sulfonamide; N-(3-(6-(1H-benzo[d]imidazol-1-yl)quinazolin-4-ylamino)-2,4-difluorophenyl)propane-1-sulfonamide; N-(2,4-difluoro-3-(6-(2-fluoropyridin-3-yl)quinazoline-4-carbonyl)phenyl) propane-1-sulfonamide; N-(3-(6-ethynylquinazolin-4-ylamino)-2,4-difluorophenyl)propane-1-sulfonamide; N-(3-(6-(2-aminopyrimidin-5-yl)quinazolin-4-ylamino)-2,4-difluorophenyl)propane-1-sulfonamide; N-(3-(6-(2-(dimethylamino) pyrimidin-5-yl)quinazolin-4-ylamino)-2,4-difluorophenyl)propane-1-sulfonamide; N-(3-(6-(1H-1,2,3-triazol-4-yl)quinazolin-4-ylamino)-2,4-difluorophenyl) propane-1-sulfonamide; N-(2,4-difluoro-3-((6-(2-fluoropyridin-3-yl)quinazolin-4-yl)(methyl)amino)phenyl)-N-methylpropane-1-sulfonamide; N-(3-(6-(6-(dimethylamino)pyridin-3-yl)quinazolin-4-ylamino)-2,4-difluorophenyl)propane-1-sulfonamide; N-(2,4-difluoro-3-(6-(2-fluoropyridin-3-yl)quinazolin-4-ylamino)phenyl) propanesultam; N-(2,4-difluoro-3-(5-fluoro-6-(2-fluoropyridin-3-yl)quinazolin-4-ylamino)phenyl)propane-1-sulfonamide; N-(3-(6-(2-chloropyridin-3-yl)quinazolin-4-ylamino)-2,4-difluorophenyl)propane-1-sulfonamide, N-(2,4-difluoro-3-(6-(6-methoxy-5-nitropyridin-3-yl)quinazolin-4-ylamino)phenyl)propane-1-sulfonamide, N-(3-(6-(3-aminophenyl)quinazolin-4-ylamino)-2,4-difluorophenyl) propane-1-sulfonamide, N-(3-(6-(5-amino-6-methoxypyridin-3-yl)quinazolin-4-ylamino)-2,4-difluorophenyl) propane-1-sulfonamide, N-(3-(6-(6-aminopyridin-2-yl)quinazolin-4-ylamino)-2,4-difluorophenyl)propane-1-sulfonamide, N-(2,4-difluoro-3-(6-(6-(trifluoromethyl)pyridin-2-yl)quinazolin-4-ylamino) phenyl)propane-1-sulfonamide, N-(3-(6-(6-cyanopyridin-2-yl)quinazolin-4-ylamino)-2,4-difluorophenyl)propane-1-sulfonamide, N-(3-(6-(2-cyanopyridin-3-yl)quinazolin-4-ylamino)-2,4-difluorophenyl)propane-1-sulfonamide, N-(2,4-difluoro-3-(6-(5-(trifluoromethyl)pyridin-3-yl) quinazolin-4-ylamino)phenyl)propane-1-sulfonamide, N-(2,4-difluoro-3-(6-(4-fluoropyridin-3-yl) quinazolin-4-ylamino)phenyl)propane-1-sulfonamide, N-(3-(6-(6-amino-5-methyl pyridin-3-yl)quinazolin-4-ylamino)-2,4-difluorophenyl)propane-1-sulfonamide.

In accordance with some embodiments of the invention, the compound have the following structures represented by formula (I):

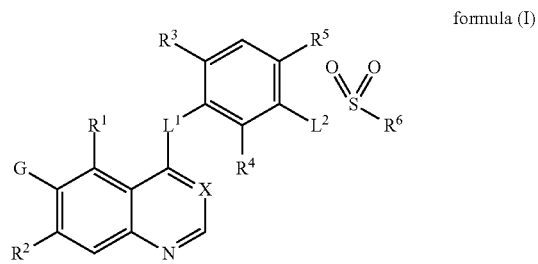

formula (I)

wherein G is selected from one of the following:

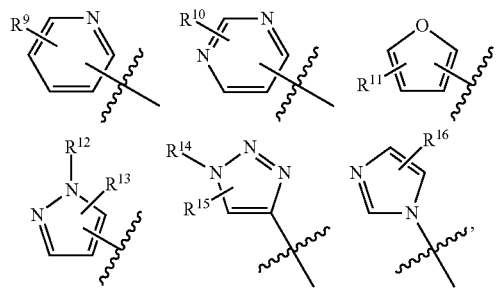

wherein

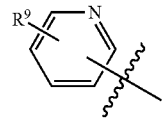

represents a pyridine optionally substituted with one or more $R^9$,

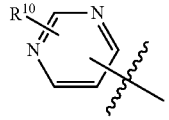

represents a pyrimidine optionally substituted with one or more $R^{10}$,

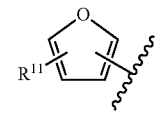

represents a furan optionally substituted with one or more $R^{11}$,

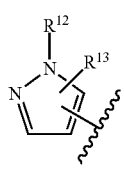

represents a pyrazole optionally, independently substituted with $R^{12}$ and one or more $R^{13}$,

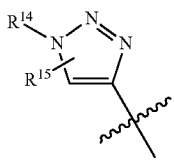

represents a triazole optionally, independently substituted with $R^{14}$ and one or more $R^{15}$,

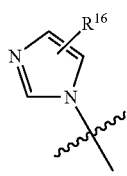

represents an imidazole optionally substituted with one or more $R^{16}$, wherein $R^9$ is independently selected from the group consisting of hydrogen, halogen, hydroxyl, amino, nitro, cyano, haloalkane, alkoxy, methoxy alkoxy, dialkylamino alkoxy, dialkylamino, and heterocyclyl, wherein $R^{10}$ is independently hydrogen, hydroxyl, amino, or dialkylamino, wherein $R^{11}$, $R^{13}$, $R^{15}$ and $R^{16}$ are independently hydrogen, halogen, or alkyl, and wherein $R^{12}$, $R^{14}$ are independently hydrogen, alkyl, or alkanoyl.

In accordance with some embodiments of the invention, the compounds have the structures represented by formula (I):

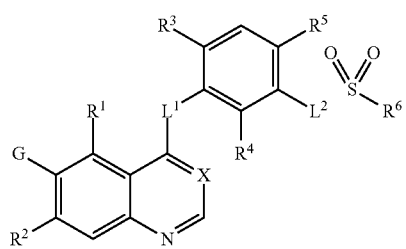

formula (I)

wherein G is selected from:

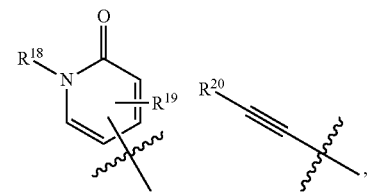

wherein

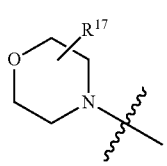

represents a morpholine optionally substituted with one or more $R^{17}$,

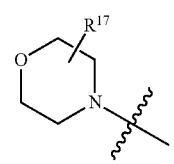

represents a pyridone optionally independently substituted with $R^{18}$ and one or more $R^{19}$,

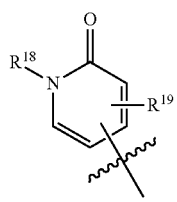

represents an alkyne optionally substituted with one or more $R^{20}$.

wherein $R^{17}$ is independently selected from the group consisting of hydrogen, halogen, hydroxyl, amino, cyano, alkyl, and alkoxy;

wherein $R^{18}$ is selected from the group consisting of hydrogen and alkyl; wherein $R^{19}$ is independently selected from the group consisting of hydrogen, halogen, hydroxyl, amino, cyano, alkyl, and alkoxy; and wherein $R^{20}$ is selected from the group consisting hydrogen, alkyl, aryl, methoxy, and alkoxy.

Other aspects and advantages of the invention will be apparent from the following description and the appended claims.

DETAILED DESCRIPTION

Definition

The term "alkyl" refers to a straight or branched monovalent saturated hydrocarbon containing, unless otherwise stated, 1-20 carbon atoms. The numerical ranges in this description are intended to include any number(s) in the defined range, as if the individual numbers have been separately discloses. For example, an alkyl group of 1-20 carbons would include $C_1, C_2, \ldots C_{20}$, as well as $C_1$-$C_{20}$, $C_1$-$C_{15}$, $C_1$-$C_{10}$, $C_1$-$C_6$, $C_1$-$C_4$, etc. Examples of alkyl include, but are not limited to, methyl, ethyl, n-propyl, i-propyl, n-butyl, i-butyl, and t-butyl. The term "alkenyl" refers to a straight or branched monovalent hydrocarbon containing 2-20 carbon atoms (e.g., $C_2$-$C_{10}$) and one or more double bonds. Examples of alkenyl include, but are not limited to, ethenyl, propenyl, allyl, and 1,4-butadienyl. The term "alkynyl" refers to a straight or branched monovalent hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. The term "alkoxy" refers to an —O-alkyl radical, wherein the alkyl portion is as defined above. Examples of alkoxy include, but are not limited to, methoxy, ethoxy, n-propoxy, iso-propoxy, n-butoxy, iso-butoxy, sec-butoxy, and tert-butoxy. The term "acyloxy" refers to an —O—C(O)—R radical in which R can be H, alkyl, alkenyl, alkynyl, cycloalkyl, cycloalkenyl, heterocycloalkyl, heterocycloalkenyl, aryl, or heteroaryl. The term "amino" refers to $NH_2$. The term "alkylamino" refers to an —N(R)-alkyl radical in which R can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent saturated hydrocarbon ring system having 3 to 30 carbon atoms (e.g., $C_3$-$C_6$ or $C_3$-$C_{12}$). Examples of cycloalkyl include, but are not limited to, cyclopropyl, cyclobutyl, cyclopentyl, cyclohexyl, cycloheptyl, cyclooctyl, and adamantanyl. The term "cycloalkenyl" refers to a monovalent non-aromatic hydrocarbon ring system having 3 to 30 carbons (e.g., $C_3$-$C_6$ or $C_3$-$C_{12}$) and one or more double bonds. Examples include cyclopentenyl, cyclohexenyl, and cycloheptenyl. The term "heterocycloalkyl" refers to a monovalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, piperidinyl, dioxanyl, morpholinyl, and tetrahydrofuranyl. The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, or 14-carbon tricyclic aromatic ring system. Examples of aryl groups include, but are not limited to, phenyl, naphthyl, and anthracenyl. The term "aryloxyl" refers to an —O-aryl. The term "arylamino" refers to an —N(R)-aryl, wherein R can be H, alkyl, alkenyl, alkynyl, cycloalkyl, cycloalkenyl, heterocycloalkyl, heterocycloalkenyl, aryl, or heteroaryl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, thiazolyl, pyrrolyl, isoquinolinyl, purinyl, oxazolyl, pyrazolyl, and carbazolyl.

Alkyl, alkenyl, alkynyl, cycloalkyl, heterocycloalkyl, cycloalkenyl, heterocycloalkenyl, amino, alkylamino, arylamino, alkoxy, aryloxy, aryl, and heteroaryl mentioned above may be substituted or unsubstituted moieties. Possible substituents on amino, alkylamino, arylamino, alkoxy, aryloxy, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)$NH_2$), carboxyl (—COOH), and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The following reaction schemes, Reaction Scheme 1 through Reaction Scheme 14, provide representative procedures that are used to prepare the compounds of Formula (I). However, one skilled in the art would appreciate that these are for illustration only and that modifications or variations are possible without departing from the scope of the invention. A quinazoline compound synthesized in accordance with embodiments of the invention may be purified by flash column chromatography, high performance liquid chromatography, crystallization, or any other suitable methods.

Intermediate I

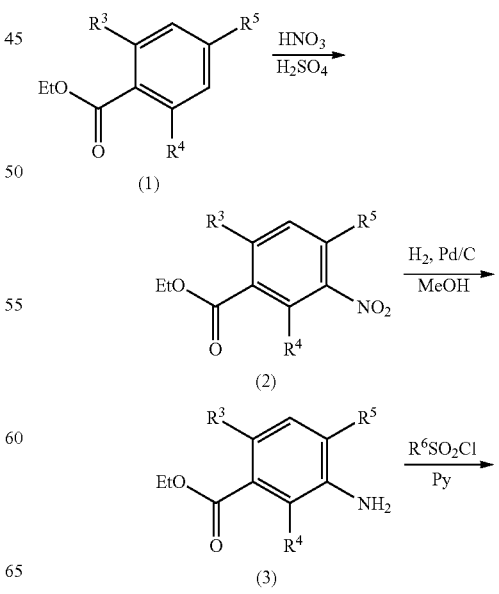

Reaction Scheme 1.

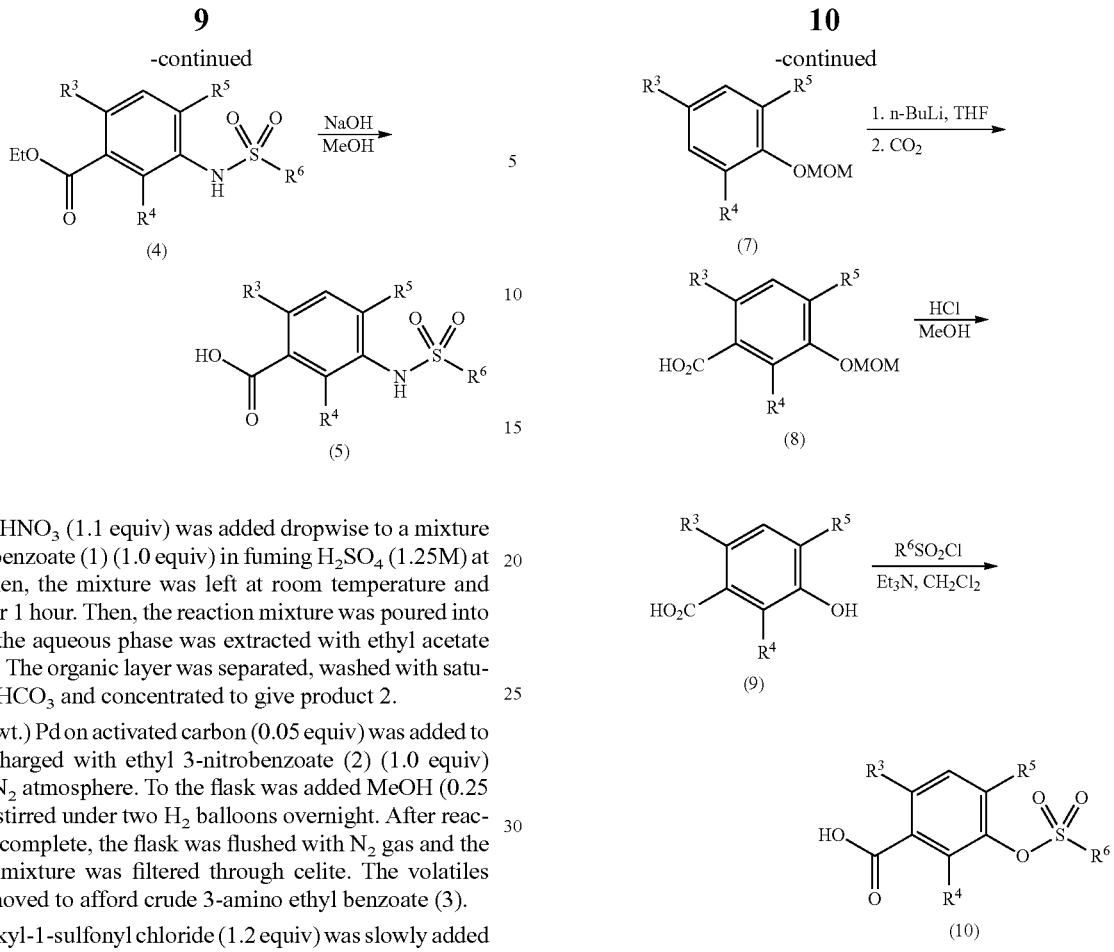

Conc. HNO₃ (1.1 equiv) was added dropwise to a mixture of ethyl benzoate (1) (1.0 equiv) in fuming H₂SO₄ (1.25M) at 0° C. Then, the mixture was left at room temperature and stirred for 1 hour. Then, the reaction mixture was poured into ice, and the aqueous phase was extracted with ethyl acetate (EtOAc). The organic layer was separated, washed with saturated NaHCO₃ and concentrated to give product 2.

10% (wt.) Pd on activated carbon (0.05 equiv) was added to a flask charged with ethyl 3-nitrobenzoate (2) (1.0 equiv) under a N₂ atmosphere. To the flask was added MeOH (0.25 M), and stirred under two H₂ balloons overnight. After reaction was complete, the flask was flushed with N₂ gas and the reaction mixture was filtered through celite. The volatiles were removed to afford crude 3-amino ethyl benzoate (3).

The alkyl-1-sulfonyl chloride (1.2 equiv) was slowly added to a solution of 3-amino ethyl benzoate (3) (1.1 equiv) in pyridine (0.5 M) maintained in a cool water bath. The reaction mixture was stirred for 1 hour at room temperature and then poured into cold water. The aqueous phase was extracted with EtOAc. The organic layer was separated, washed with saturated NH₄Cl and brine, then dried in MgSO₄, filtered, and concentrated to give 3-(N-(alkylsulfonyl) sulfonamido) ethyl benzoate (4).

A 1N aqueous NaOH solution (3.0 equiv) was added to a solution of 3-(N-(alkylsulfonyl)sulfonamido)ethyl benzoate (4) (1.0 equiv) in 4:1 THF/MeOH (0.2M). The reaction mixture was stirred at room temperature overnight. The majority of the organic solvents were removed in vacuo. 1N HCl was slowly added to the mixture, and the resulting solid was filtered and rinsed with water. The material was washed with Et₂O to give 3-alkylsulfonamido benzoic acid (5).

Intermediate II

Reaction Scheme 2.

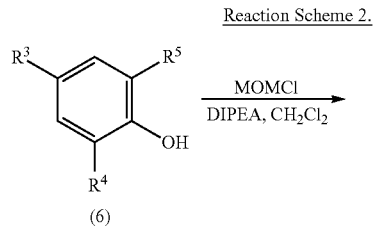

N,N-Diisopropylethylamine (2.0 equiv) and chloromethyl methyl ether (2.0 equiv) were added to a solution of phenol (6) (1.0 equiv) in dry CH₂Cl₂ under N₂ atmosphere at 0° C. The resulting yellow mixture was stirred for 30 min at 0° C. and then left overnight at room temperature. The organic mixture was diluted with aqueous 10% NaOH and extracted with dichloromethane. The organic layers were combined, dried over MgSO₄, filtered, and concentrated in vacuo. The crude product was purified on a silica column. Elution with ethyl acetate in hexane afforded the desired product 7.

To a solution of methoxymethoxy benzene (7) (1.0 equiv) in THF (0.35 M) under nitrogen at −70° C. was added a solution of 1.4 M n-butyllithium in hexanes (0.99 equiv) dropwise over 10 min. The mixture was stirred at −70° C. for 1.5 hr and was then decanted onto pulverized dry ice. Once the effervescence had subsided, the mixture was allowed to warm to RT and water was added. The aqueous solution was extracted twice with ether and was then acidified to pH 1 by the addition of concentrated hydrochloric acid. The resulting suspension was sonicated for 5 min and was then extracted twice with CH₂Cl₂. The combined CH₂Cl₂ extracts were dried with MgSO₄ and evaporated in vacuo to afford product 9.

Alkyl sulfonyl chloride (1.2 equiv) was slowly added to a solution of 3-hydroxy benzoic acid (9) (1.0 equiv) in pyridine (0.5 M) maintained in a cool water bath. The reaction mixture was stirred for 1 hour at room temperature. Water was added and the organic layer was separated, washed with water and brine, then dried with MgSO$_4$, filtered and concentrated to afford product 10.

Intermediate III

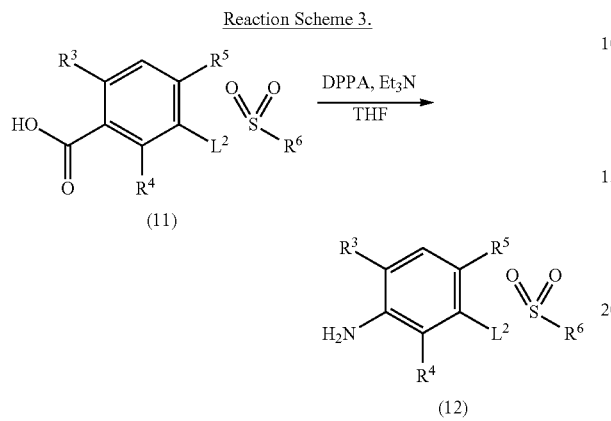

Reaction Scheme 3.

To a solution of benzoic acid (11) (1 equiv) in THF (0.25 M) was added triethylamine (2.3 equiv) and diphenylphosphonic azide (1.15 equiv). The reaction mixture was stirred at room temperature for 3 hours and then warmed to 80° C. for 2 hours. Water was added, and the mixture stirred at 80° C. for 15 hours. The reaction mixture was diluted with EtOAc, and the organic layer was washed with saturated aq. NaHCO$_3$ solution and brine. The solvent was removed under reduced pressure and the residual purified via silica gel column chromatography to give compound 12.

Intermediate IV

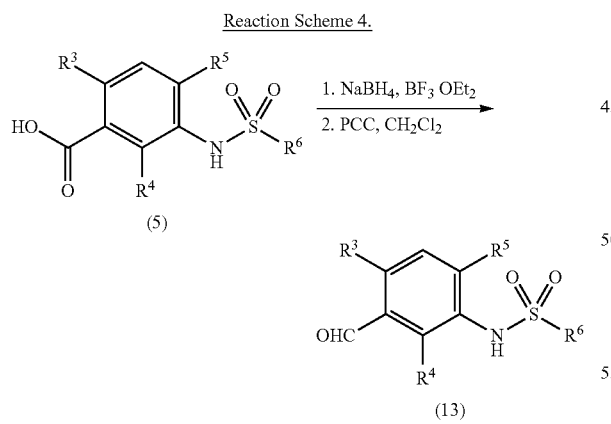

Reaction Scheme 4.

To a stirred solution of 3-alkylsulfonamido benzoic acid (5) (1 equiv) in anhydrous THF (1.1 M) at −20° C., lithium aluminum hydride (3.85 equiv) was added in small portions and the reaction was stirred at −20° C. for 4 h followed by 1 h at room temperature. Then, the reaction was quenched with saturated aqueous NH$_4$Cl. Usual work-up gave a crude product, which was dried under vacuum and dissolved in anhydrous CH$_2$Cl$_2$ at 0° C., and then pyridinium chlorochromate (2.0 equiv) was added. The reaction mixture was stirred for 40 min in an ice bath and then diluted with saturated aqueous NaHCO$_3$, and extracted with EtOAc. The combined organic layers were washed with water and brine, dried over anhydrous MgSO$_4$, and evaporated in vacuo. Column chromatography on silica gel with EtOAc in hexane yielded product 13.

Intermediate V

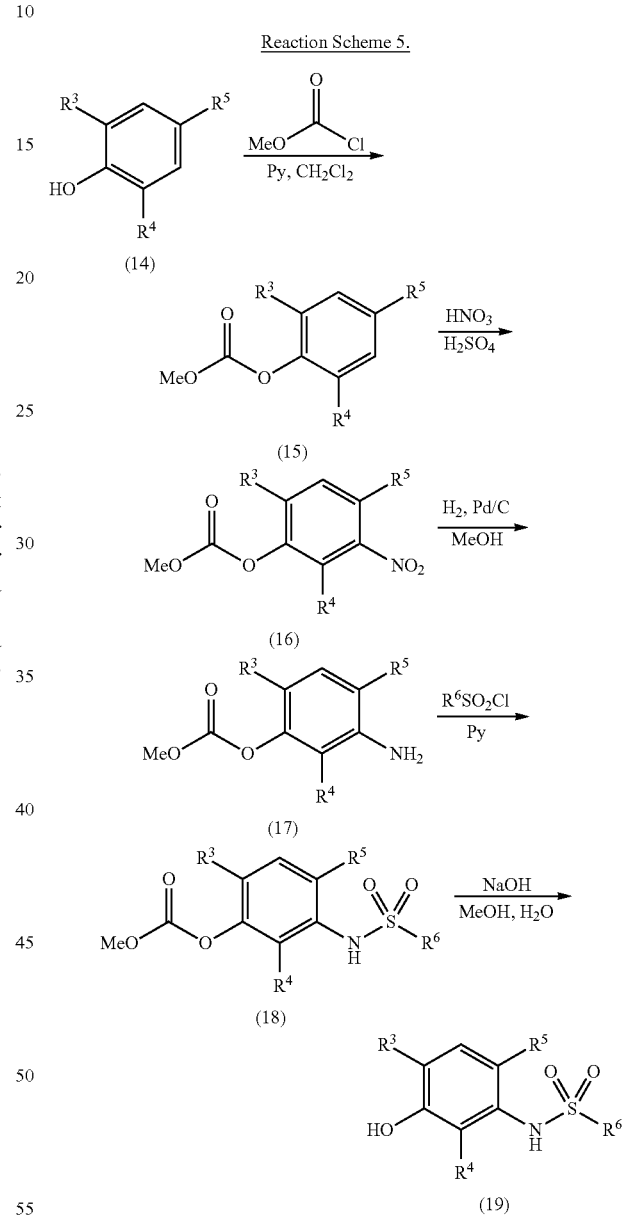

Reaction Scheme 5.

To a stirred solution of phenol (14) (1.0 equiv) in dichloromethane (0.5 M) at 0° C. was added pyridine (1.05 equiv) and stirred for 10 minutes. Methyl chloroformate (1.05 equiv) diluted in CH$_2$Cl$_2$ was added dropwise during 15 minutes and the reaction mixture allowed to warm-up to room temperature and the stirring continued for 17 hrs. The reaction mixture was diluted with CH$_2$Cl$_2$ and washed with 0.5 N NaOH solution in water followed by brine. The organic layer was filtered through a bed of anhydrous MgSO$_4$, concentrated to dryness to afford product 15.

Phenyl methyl carbonate (15) (1.0 equiv) was dissolved in concentrated sulfuric acid under N$_2$ and cooled to 0° C. KNO$_3$ (2.0 equiv) was then added cautiously, while keeping the temperature around 0° C. The mixture was then allowed to stir for 2 hrs while warming up to room temperature. Then, it was poured onto ice cautiously and extracted with ether twice. Organics were combined, dried on MgSO$_4$ and concentrated under reduced pressure to give the product 16.

To a solution of 3-nitrophenyl methyl carbonate (16) (1.0 equiv) in methanol (0.2 M) was added 20% palladium on carbon (10% wt). The reaction mixture was stirred under a H$_2$ atmosphere at room temperature for overnight. After nitrogen replacement, the catalyst was filtered off. The solvent was evaporated from the filtrate under reduced pressure, and the residue was recrystallized from diethyl ether to give the title compound 17.

Alkyl-1-sulfonyl chloride (1.2 equiv) was slowly added to a solution of ethyl 3-amino benzoate (17) (1.0 equiv) in pyridine (0.5 M) maintained in a cool water bath. The reaction mixture was stirred for 1 hour at room temperature. Water was added and the organic layer was separated, washed with water and brine, then dried with MgSO$_4$, filtered and concentrated to afford product 18.

A solution of phenyl methyl carbonate (18) (1.0 equiv) in methanol (0.2 M) was treated with a 1 N sodium hydroxide (5.0 equiv) solution, and heated at 75° C. for 14 hours. After cooling to room temperature, the methanol was evaporated in vacuo. The resulting aqueous mixture was acidified with a 1 N hydrochloric acid solution, diluted with brine and extracted with dichloromethane. The combined organic phase was dried over anhydrous MgSO$_4$, filtered, and concentrated. The solid was purified by filtration through a short column of silica gel, eluding with ethyl acetate, to yield the title compound 19.

Intermediate VI

Reaction Scheme 6.

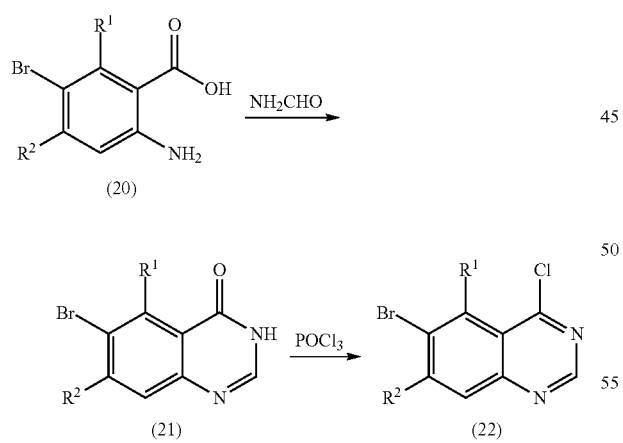

A suspension of compound 20 (1.0 equiv) in formamide (15.0 equiv) was heated at 165° C. for 6 hours. After cooling to room temperature, water was added to the reaction mixture. The precipitate was collected by filtration, washed with water and dried in 120° C. oven, yielding the title compound 21.

A suspension of compound 21 (1.0 equiv) in POCl$_3$ (1.0 M) was heated to reflux for 6 hours. The resulting clear solution was then cooled to room temperature and concentrated in vacuo to afford 4-chloro-6-bromoquinazoline (22), which was carried to the next step without further purification.

Intermediate VII

Reaction Scheme 7.

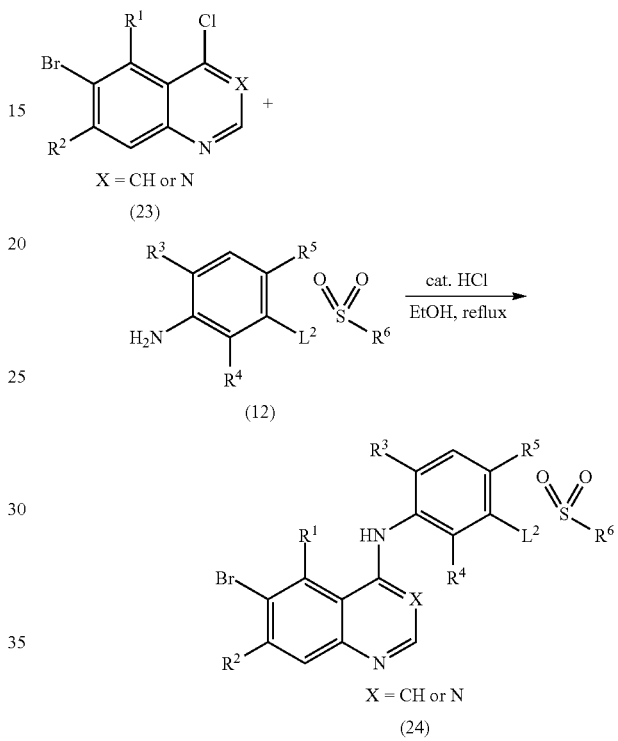

To a solution of compound 23 (1.0 equiv) in ethanol (0.5 M) was added compound 12 (1.1 equiv) and catalytic amount hydrochloric acid. After reflux for 2 hours, the reaction mixture was allowed to cool to room temperature and concentrated in vacuo. The resulting residue was diluted with 100 ml ethyl acetate, washed with sat. NaHCO$_3$ (aq.) and brine, dried over MgSO$_4$, and concentrated in vacuo to afford the title product. Further purification by column chromatography gave the compound 24.

Intermediate VIII

Reaction Scheme 8.

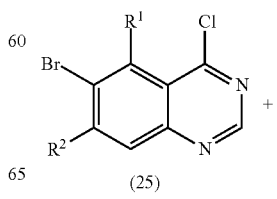

-continued

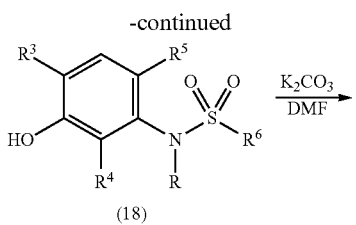
(18)

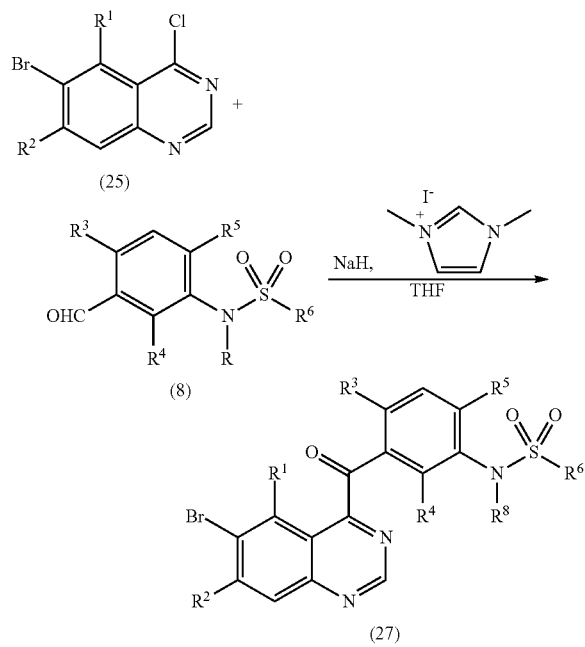

To a stirred solution of 3-alkylsulfonamidephenol (18) (1.1 equiv) and 4-chloroquinazoline (25) (1.0 equiv) in DMF (0.3 M) was added 60% oil suspension sodium hydride (1.25 equiv) at 0° C. Then, the reaction mixture was allowed to warm to room temperature and stirred for 5 h. The reaction was quenched by slowly adding water and diluted with ethyl acetate. It was washed with water, brine, dried over anhydrous MgSO$_4$, filtered and concentrated. Further purification by column chromatography gave the compound 26.

Reaction Scheme 9.

Intermediate IX

Sodium hydride (50% in oil, 1.3 equiv) was added to a solution of 4-chloroquinazoline (25) (1.0 equiv), benzaldehyde (8) (1.3 equiv) and 1,3-dimethylimidazolium iodide (0.33 equiv) in THF. The mixture was refluxed for an appropriate time in an oil bath with stirring. After cooling, the mixture was poured onto an ice-H$_2$O mixture, and extracted with ethyl acetate. The extract was dried over MgSO$_4$ and concentrated to dryness. Further purification by column chromatography gave the compound 27.

Final Product I

Reaction Scheme 10.

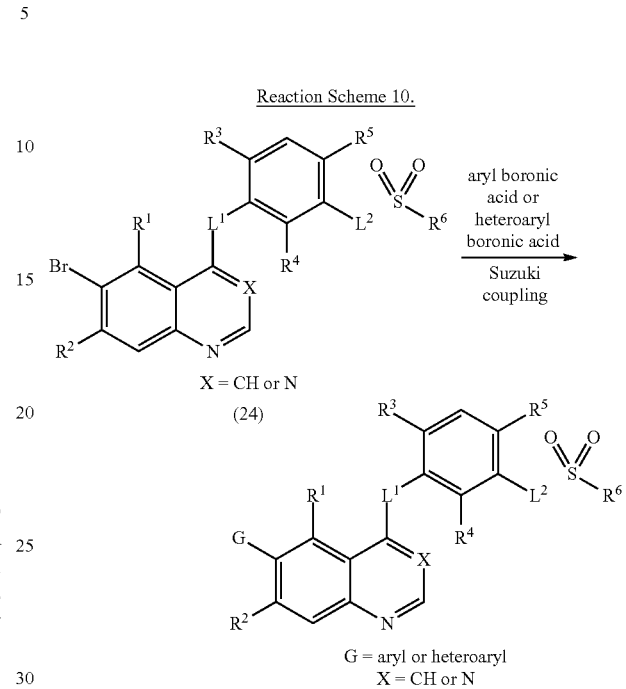

Compound 24 (1.0 equiv), heteroaryl boronic acid (1.5 equiv) and Na$_2$CO$_3$ (3.0 equiv) in dioxane/H$_2$O (4:1, 0.2 M) were treated with Pd(Ph$_3$P)$_4$ (0.05 equiv). The reaction was stirred at 80° C. for 2 h. The crude reaction mixture was filtered, dried over MgSO$_4$, and concentrated under reduced pressure. Further purification by column chromatography gave the compound 28.

Final Product II

Reaction Scheme 11.

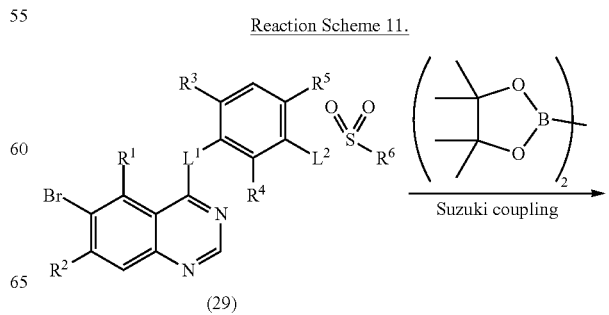

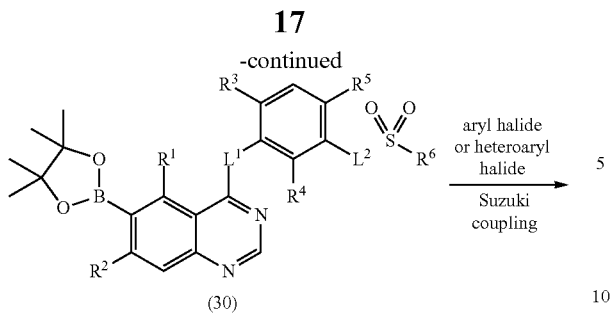

Compound 29 (1.0 equiv), potassium acetate (3.0 equiv), Pd(dppf)Cl$_2$ (0.03 equiv) and bis-pinacolatodiboron (1.2 equiv) were added to dioxane (0.3 M) and heated 5 h to 80° C. The solution was extracted with ethyl acetate and water and the organic phase washed with water again, dried over MgSO$_4$ and evaporated to low bulk. Further purification by column chromatography gave the compound 30.

Dioxaborolan quinazolin (30) (1.0 equiv), aryl halide or heteroaryl halide (1.2 equiv), tetrakis(triphenylphosphine)palladium(O) (0.05 equiv) and 2.0 M aqueous sodium carbonate (2.5 equiv) were added to dioxane (0.3 M) and heated 5 h to 80° C. The solution was extracted with ethyl acetate and water and the organic phase washed with water again, dried over MgSO$_4$ and evaporated to low bulk. Further purification by column chromatography gave the compound 31.

Final Product III

Reaction Scheme 12.

A flask was charged with CuI (0.1 equiv), L-proline (0.2 equiv), K$_2$CO$_3$ (2 equiv), compound 29 (1.0 equiv), and imidazole (1.5 equiv), evacuated, and backfilled with nitrogen. To this mixture was added DMSO (0.2 M) by syringe at room temperature under nitrogen. The mixture was heated at 100° C. before it was partitioned between water and ethyl acetate. The organic layer was separated, and the aqueous layer was extracted with ethyl acetate. The combined organic layers were washed with brine, dried over MgSO$_4$, and concentrated in vacuo. Further purification by column chromatography gave the compound 32.

Final Product IV

Reaction Scheme 13.

Tetrakis(triphenylphosphine)palladium (0.02 equiv) was added to a solution of compound 29 (1.0 equiv), propargyl alcohol (1.5 equiv) and triethylamine (1.5 equiv) in THF (0.2 M) and the solution heated to reflux for 16 hours. The mixture was cooled then filtered through celite, eluting with methanol. Further purification by column chromatography gave the compound 33.

Final Product V

Reaction Scheme 14.

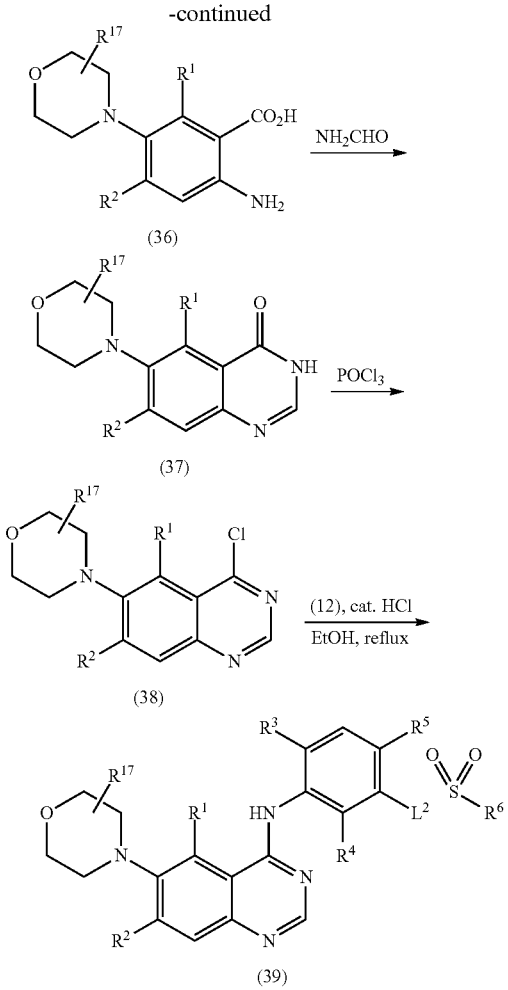

Morpholine (0.5 M) was added to a solution of 5-fluoro-2-nitrobenzoic acid (1.0 equiv) and the reaction was heated to 90° C. for 5 hours. The reaction was cooled and water was added. After stirring for 10 minutes the mixture was filtered and the filter cake was washed with water. Citric acid was charged to the filtrate, causing more of the product to precipitate. The filter cake was washed with water then dried overnight at 40° C. under vacuum to give product 35.

10% (wt.) Pd on activated carbon (0.05 equiv) was added to a flask charged with 2-nitrobenzoic acid (35) (1.0 equiv) under a $N_2$ atmosphere. To the flask was added MeOH (0.25 M), and stirred under two $H_2$ balloons overnight. After reaction complete, the flask was flushed with $N_2$ gas, and the reaction mixture was filtered through celite. The volatiles were removed to afford crude 2-amino benzoic acid (36).

A suspension of compound 36 (1.0 equiv) in formamide (7.0 equiv) was heated at 165° C. for 6 hours. After cooling to room temperature, ethyl acetate was added to the reaction mixture and stirred vigorously. The precipitate was collected by filtration, washed with ethyl acetate and dried in 120° C. oven, yielding the title compound 37.

A suspension of compound 37 (1.0 equiv) in $POCl_3$ (1.0 M) was heated to reflux for 6 hours. The resulting clear solution was then cooled to room temperature and concentrated in vacuo to afford crude product 37 which was carried to the next step without further purification.

To a solution of compound 38 (1.0 equiv) in ethanol (0.5 M) was added compound 12 (1.1 equiv) and catalytic amount hydrochloric acid. After reflux for 4 hours, the reaction mixture was allowed to cool to room temperature and concentrated in vacuo. The resulting residue was diluted with 100 ml ethyl acetate, washed with sat. $NaHCO_3$ (aq.) and brine, dried over $MgSO_4$, and concentrated in vacuo to afford the title product. Further purification by column chromatography gave the compound 39.

The quinazoline compounds mentioned herein may contain a non-aromatic double bond and one or more asymmetric centers, e.g., in the substituents attached to the core aromatic rings. Therefore, these compounds may occur as racemates and racemic mixtures, single enantiomers, individual diastereomers, diastereomeric mixtures, and cis- or trans-isomeric forms. All such isomeric forms are within the scope of the invention. The quinazoline compounds of the invention may have acidic or basic functional groups (e.g., on the substitution groups) that may form salts, particularly pharmaceutically acceptable salts. Formation of such salts is a routine practice in the pharmaceutical industry. Such quinazoline salts are within the scope of the invention. Similarly, the acidic or basic groups may be functionalized, for example into esters. Such functionalized derivatives will be hydrolyzed in vivo. Therefore, such derivatives may function as pro-drugs of the quinazoline compounds of the invention. Formation of pro-drugs involves only routine skills and one skilled in the art would know how to prepare and use such pro-drugs without undue experimentation.

Also within the scope of this invention are (1) a pharmaceutical composition that contains an effective amount of at least one of the quinazoline compounds of this invention and a pharmaceutically acceptable carrier, (2) a method for treating a protein kinase-related disease (e.g., cancer) by administering to a subject in need of this treatment an effective amount of such a quinazoline compound, and (3) a method of decreasing the activity of at least one protein kinase by contacting the at least one protein kinase with at least one of the quinazoline compounds of this invention.

As used herein, the term "protein kinase-related disease" refers to a disease or condition that is characterized by abnormal PK activity or a disease or condition that can be treated with changes to the activity of at least one PK. Abnormal PK activity can arise as the result of elevated PK expression level, or presence of PK expression that does not happen in normal conditions. PK-related disease describe herein include, but not limited to, cancer, diabetes, a hyper-proliferation disorder, hyperproliferative disorders of the kidney, renal disease, von Hippel-Lindau disease, restenosis, fibrosis, psoriasis, osteoarthritis, rheumatoid arthritis, an inflammatory disorder, immunological disorders such as autoimmune diseases (e.g., AIDS, lupus, etc.), cardiovascular disorders (e.g. atherosclerosis), and blood vessel proliferative disorders such as abnormal vasculogenesis.

The term "treating" refers to administering a quinazoline compound to a subject that has a protein kinase-related disease, or has a symptom of or a predisposition toward it, with the purpose to cure, heal, alleviate, relieve, alter, remedy, ameliorate, improve, affect or reduce the risk of the disorder, the symptoms of or the predisposition toward the disorder. For example, treating cancer refers to the treatment results in inhibition of cancer growth or cancer cell growth, regression in cancer growth (i.e. it reduces the size of a detectable cancer), or the disappearance of a cancer.

The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents. Determination of an effective amount requires only routine skill and one skilled in the art would be able to determine such effective amounts for the intended use without undue experimentation. The subject in need of the treatment can be a mammal. The term "mammal" refers to human or nonhuman mammal, for example, dogs, cats, pigs, cows, sheep, goats, horses, rats, or mice.

Cancer that can be treated by the methods of the invention includes any abnormal cell or tissue growth, for example, a tumor, whether malignant, pre-malignant, or non-malignant. Cancer is characterized by uncontrolled proliferation of cells that may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more neoplastic cell type. The term cancer includes, as non-limiting examples, lung cancer, colon cancer, colorectal cancer, breast cancer, prostate cancer, liver cancer, pancreatic cancer, bladder cancer, gastric cancer, renal cancer, salivary gland cancer, ovarian cancer, uterine body cancer, cervical cancer, oral cancer, skin cancer, brain cancer, lymphoma, and leukemia. It also includes drug resistant cancer (including but not limited to multidrug resistant cancer).

The compounds described herein can be administered to a mammal in conjunction with radiation therapy, immunotherapy, monoclonal antibody therapy, hormonal therapy, chemotherapy using other agents, and/or surgery. By in conjunction with, the therapies need not occur at the same time, but can be in succession, or alternating with each other and/or periods of rest and recovery.

In one embodiment, a protein kinase-related disease, such as cancer, is treated with a method comprising administering an effective amount of at least one quinazoline compound of this invention and at least one chemotherapeutic agent to a mammal. Nonlimiting examples of chemotherapeutic agent include, PK inhibitors other than the compound described herein (e.g., imatinib mesylate, gefitinib, dasatinib, erlotinib, lapatinib, sunitinib, nilotinib, and sorafenib; antibodies, including, e.g., trastuzumab, rituximab, cetuximab, and bevacizumab; mitoxantrone; dexamethasone; prednisone; and temozolomide), alkylating agents (e.g., melphalan, chlorambucil, busulfan, thiotepa, ifosfamide, carmustine, lomustine, semustine, streptozocin, decarbazine, and cyclophosphamide), mitotic inhibitors, antimetabolites (e.g., capecitibine, gemcitabine, 5-fluorouracil or 5-fluorouracil/leucovorin, fludarabine, cytarabine, mercaptopurine, thioguanine, pentostatin, and methotrexate), cell cycle inhibitors, enzymes, hormones, anti-hormones, growth-factor inhibitors, plant alkaloids and terpenoids, topoisomerase inhibitors (e.g., etoposide, teniposide, camptothecin, topotecan, irinotecan, doxorubicin, and daunorubicin), antitumor antibiotics (e.g., actinomycin D, bleomycin, mitomycin C, adriamycin, daunorubicin, idarubicin, doxorubicin and pegylated liposomal doxorubicin), vinca alkaloids (e.g., vincristine and vinblastin), taxanes (e.g., paclitaxel and docetaxel), platinum agents (e.g., cisplatin, carboplatin, and oxaliplatin), thalidomide and related analogs (e.g., CC-5013 and CC-4047), monoclonal antibodies, and antiangiogenic agents.

As used herein, the term "contacting" means brining a compound of this invention and at least one PK together in a way that the compound can decrease the activity of the at least one PK, either directly, i.e., by acting on the protein kinase itself, or indirectly, i.e., by acting on another molecule on which the activity of the at least one PK is dependent. "Contacting" can occur in vitro or in vivo. For instance, in a test tube that contains the at least one PK; in a culture dish that has whole cells grown; or in a mammal to which the compound of this invention is administered. Examples of target PK include, but are not limited to EGFR, CDK1, Aurora A & B kinase, MAP, CDK2, Raf, NEK (including NEK 4a, NEK 4b, NEK 5 and NEK 6), BUB1, VEGFR, C-MET, HER2, HER3, HER4, IR, IGF-IR, IRR, PDGFRct, PDGFRO, CSFIR, C-Kit, C-fins, Flk-1R, Flk4, KDRlFlk-1, FLT-1, FLT3, FGFR-1, FGFR-2, FGFR-3, FGFR4, Src, Frk, Btk, Csk, Abl, ZAP70, Fes, Fps, Fak, Jak, Ack, Yes, Fyn, Lyn, Lck, Blk, Hck, Fgr, Aur2, and Yrk.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In one embodiment, a quinazoline compound of this invention is administered intravenously, suitable carriers may include but not limited to, physiological saline or phosphate buffered saline (PBS), and solutions containing thickening and solubilizing agents, such as glucose, polyethylene glycol, and polypropylene glycol and mixtures thereof.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectable, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A quinazoline compound-containing composition can also be administered in the form of suppositories for rectal administration.

A carrier in the pharmaceutical composition should be "acceptable" in the sense of being compatible with the active ingredient of the formulation (and preferably, capable of stabilizing it) and not deleterious to the subject to be treated. One or more solubilizing agents (e.g., cyclodextrin) which form more soluble complexes with the active quinazoline compounds can be utilized as pharmaceutical carriers for delivery of the active compounds. Examples of other carriers include colloidal silicon dioxide, magnesium stearate and sodium lauryl sulfate.

Suitable in vitro assays can be used to preliminarily evaluate the efficacy of the quinazoline compounds of this invention in anticancer activities such as inhibiting growth of tumor cells. The compounds can further be examined for their efficacy in treating cancer. For example, a compound can be administered to an animal (e.g., a mouse model) having cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever.

EXAMPLES

Exemplary quinazoline compounds are listed in Table 1. Their calculated mass and observed ESI-MS data are provided in Table 2.

TABLE 1

Quinazoline compounds

| Cpd. ID | Structure |
| --- | --- |
| 1 | 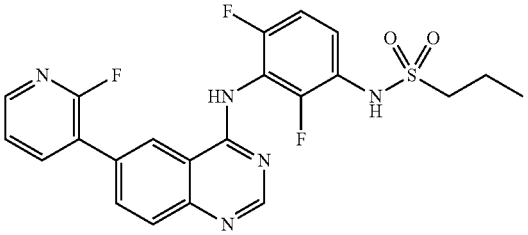<br>N-(2,4-difluoro-3-(6-(2-fluoropyridin-3-yl)quinazolin-4-ylamino)phenyl)propane-1-sulfonamide |
| 2 | 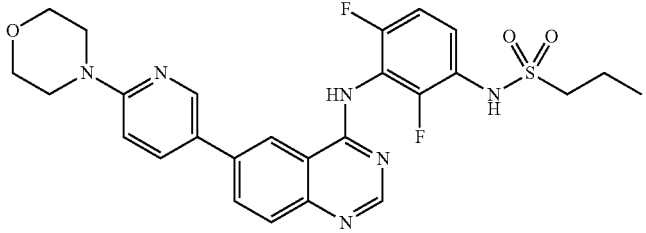 [SMILES: CCCS(=O)(=O)Nc1ccc(F)c(Nc2ncnc3ccc(-c4ccc(N5CCOCC5)nc4)cc23)c1F]<br>N-(2,4-difluoro-3-(6-(6-morpholinopyridin-3-yl)quinazolin-4-ylamino)phenyl)propane-1-sulfonamide |
| 3 | 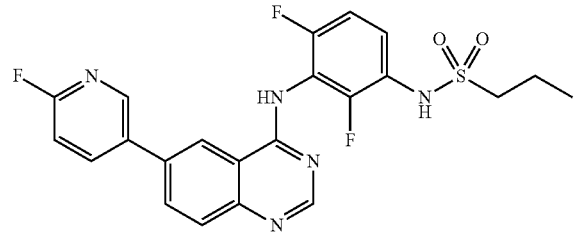 [SMILES: CCCS(=O)(=O)Nc1ccc(F)c(Nc2ncnc3ccc(-c4ccc(F)nc4)cc23)c1F]<br>N-(2,4-difluoro-3-(6-(6-fluoropyridin-3-yl)-quinazolin-4-ylamino)phenyl)propane-1-sulfonamide |

TABLE 1-continued

Quinazoline compounds

| Cpd. ID | Structure |
|---|---|
| 4 | 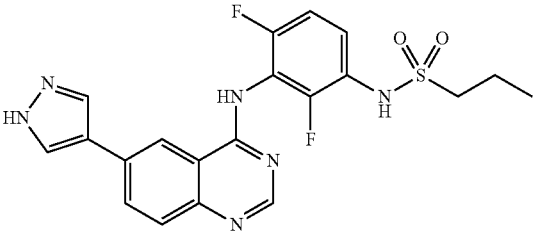 [SMILES: CCCS(=O)(=O)Nc1ccc(F)c(Nc2ncnc3ccc(-c4cn[nH]c4)cc23)c1F]<br>N-(3-(6-(1H-pyrazol-4-yl)quinazolin-4-ylamino)-2,4-difluorophenyl)propane-1-sulfonamide |
| 5 | 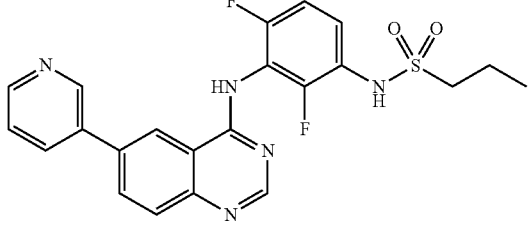<br>N-(2,4-difluoro-3-(6-(pyridin-3-yl)-quinazolin-4-ylamino)phenyl)propane-1-sulfonamide |
| 6 | 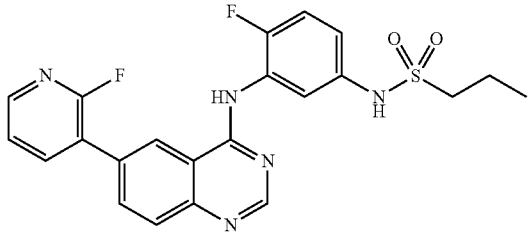 [SMILES: CCCS(=O)(=O)Nc1ccc(F)c(Nc2ncnc3ccc(-c4cccnc4F)cc23)c1]<br>N-(4-fluoro-3-(6-(2-fluoropyridin-3-yl)-quinazolin-4-ylamino)phenyl)propane-1-sulfonamide |
| 7 | 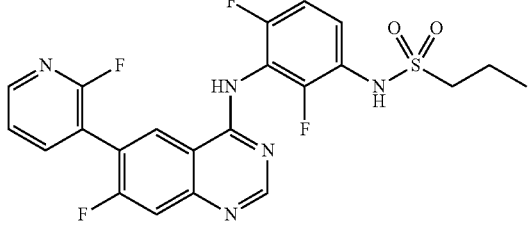<br>N-(2,4-difluoro-3-(7-fluoro-6-(2-fluoropyridin-3-yl)quinazolin-4-ylamino)phenyl)propane-1-sulfonamide |

TABLE 1-continued

Quinazoline compounds

| Cpd. ID | Structure |
|---|---|
| 8 | 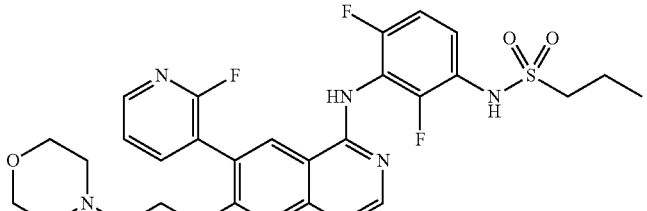<br>N-(2,4-difluoro-3-(6-(2-fluoropyridin-3-yl)-7-(2-morpholinoethoxy)quinazolin-4-ylamino)phenyl)propane-1-sulfonamide |
| 9 | 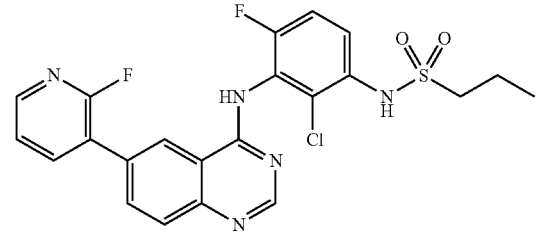 [SMILES: CCCS(=O)(=O)Nc1ccc(F)c(Nc2ncnc3ccc(-c4cccnc4F)cc23)c1Cl]<br>N-(2-chloro-4-fluoro-3-(6-(2-fluoropyridin-3-yl)quinazolin-4-ylamino)phenyl)propane-1-sulfonamide |
| 10 | 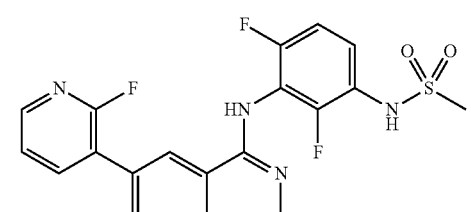<br>N-(2,4-difluoro-3-(6-(2-fluoropyridin-3-yl)quinazolin-4-ylamino)phenyl)methanesulfonamide |
| 11 | 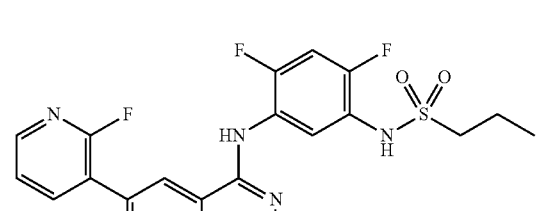<br>N-(2,4-difluoro-5-(6-(2-fluoropyridin-3-yl)-quinazolin-4-ylamino)phenyl)propane-1-sulfonamide |

TABLE 1-continued

Quinazoline compounds

| Cpd. ID | Structure |
|---|---|
| 12 | 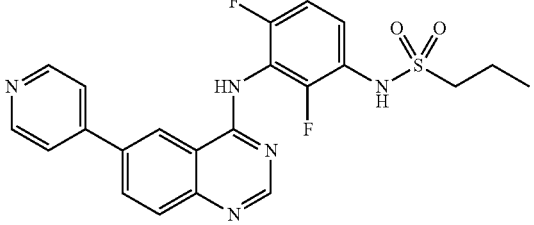<br>N-(2,4-difluoro-3-(6-(pyridin-4-yl)-quinazolin-4-ylamino)phenyl) propane-1-sulfonamide |
| 13 | 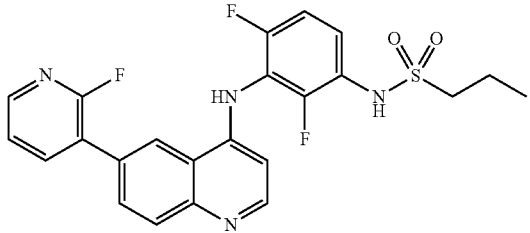 [SMILES: CCCS(=O)(=O)Nc1ccc(F)c(Nc2ccnc3ccc(-c4cccnc4F)cc23)c1F]<br>N-(2,4-difluoro-3-(6-(2-fluoropyridin-3-yl)-quinolin-4-ylamino)phenyl)propane-1-sulfonamide |
| 14 | 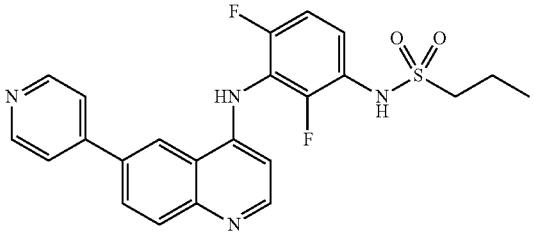 [SMILES: CCCS(=O)(=O)Nc1ccc(F)c(Nc2ccnc3ccc(-c4ccncc4)cc23)c1F]<br>N-(2,4-difluoro-3-(6-(pyridin-4-yl)quinolin-4-ylamino)phenyl) propane-1-sulfonamide |
| 15 | 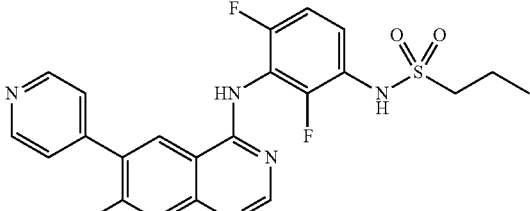<br>N-(2,4-difluoro-3-(7-fluoro-6-(pyridin-4-yl)quinazolin-4-ylamino)phenyl) propane-1-sulfonamide |

TABLE 1-continued

Quinazoline compounds

| Cpd. ID | Structure |
|---|---|
| 16 | 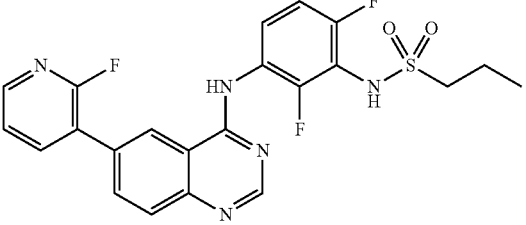<br>N-(2,6-difluoro-3-(6-(2-fluoropyridin-3-yl)quinazolin-4-ylamino)phenyl)propane-1-sulfonamide |
| 17 | 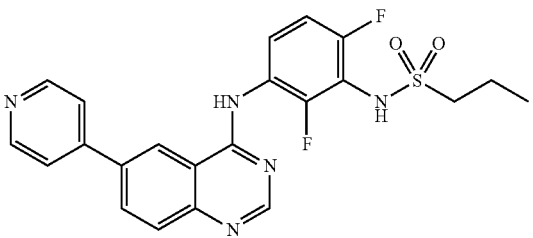 [SMILES: CCCS(=O)(=O)Nc1c(F)ccc(Nc2ncnc3ccc(-c4ccncc4)cc23)c1F]<br>N-(2,6-difluoro-3-(6-(pyridin-4-yl)quinazolin-4-ylamino)phenyl)propane-1-sulfonamide |
| 18 | 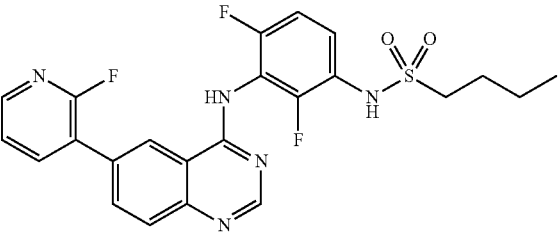 [SMILES: CCCCS(=O)(=O)Nc1ccc(F)c(Nc2ncnc3ccc(-c4cccnc4F)cc23)c1F]<br>N-(2,4-difluoro-3-(6-(2-fluoropyridin-3-yl)quinazolin-4-ylamino)phenyl)butane-1-sulfonamide |
| 19 | 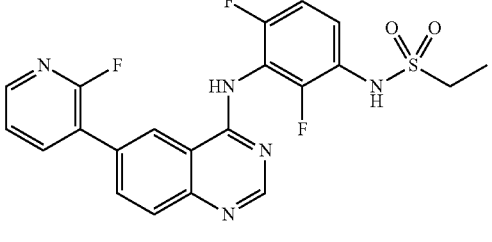<br>N-(2,4-difluoro-3-(6-(2-fluoropyridin-3-yl)quinazolin-4-ylamino)phenyl)ethanesulfonamide |

TABLE 1-continued

Quinazoline compounds

| Cpd. ID | Structure |
|---|---|
| 20 | 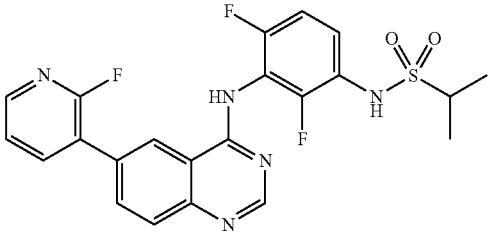 [SMILES: CC(C)S(=O)(=O)Nc1ccc(F)c(Nc2ncnc3ccc(-c4cccnc4F)cc23)c1F]  N-(2,4-difluoro-3-(6-(2-fluoropyridin-3-yl)quinazolin-4-ylamino)phenyl)propane-2-sulfonamide |
| 21 | 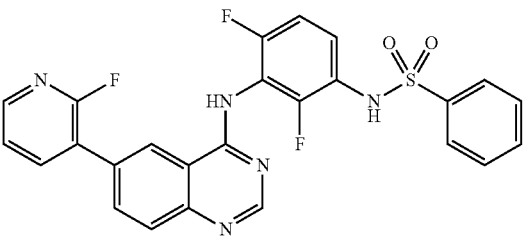 [SMILES: O=S(=O)(Nc1ccc(F)c(Nc2ncnc3ccc(-c4cccnc4F)cc23)c1F)c1ccccc1]  N-(2,4-difluoro-3-(6-(2-fluoropyridin-3-yl)quinazolin-4-ylamino)phenyl)benzenesulfonamide |
| 22 | 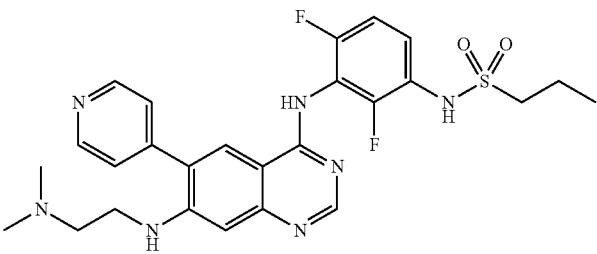 [SMILES: CCCS(=O)(=O)Nc1ccc(F)c(Nc2ncnc3cc(NCCN(C)C)c(-c4ccncc4)cc23)c1F]  N-(3-(7-(2-(dimethylamino)ethylamino)-6-(pyridin-4-yl)quinazolin-4-ylamino)-2,4-difluorophenyl)propane-1-sulfonamide |
| 23 | 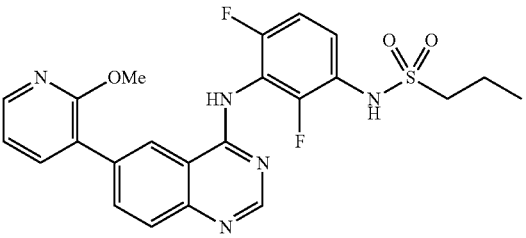 [SMILES: CCCS(=O)(=O)Nc1ccc(F)c(Nc2ncnc3ccc(-c4cccnc4OC)cc23)c1F]  N-(2,4-difluoro-3-(6-(2-methoxypyridin-3-yl)quinazolin-4-ylamino)phenyl)propane-1-sulfonamide |

TABLE 1-continued

Quinazoline compounds

| Cpd. ID | Structure |
|---|---|
| 24 | 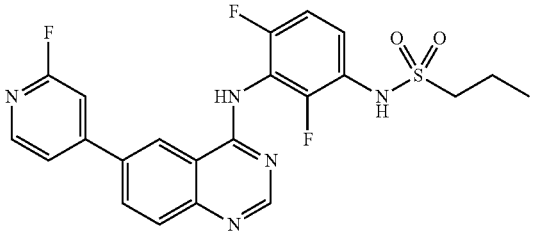 [SMILES: CCCS(=O)(=O)Nc1ccc(F)c(Nc2ncnc3ccc(-c4ccnc(F)c4)cc23)c1F]<br>N-(2,4-difluoro-3-(6-(2-fluoropyridin-4-yl)quinazolin-4-ylamino)phenyl)propane-1-sulfonamide |
| 25 | 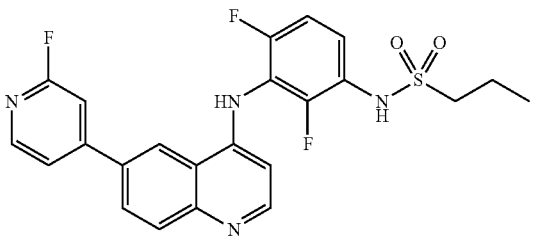 [SMILES: CCCS(=O)(=O)Nc1ccc(F)c(Nc2ccnc3ccc(-c4ccnc(F)c4)cc23)c1F]<br>N-(2,4-difluoro-3-(6-(2-fluoropyridin-4-yl)quinolin-4-ylamino)phenyl)propane-1-sulfonamide |
| 26 | 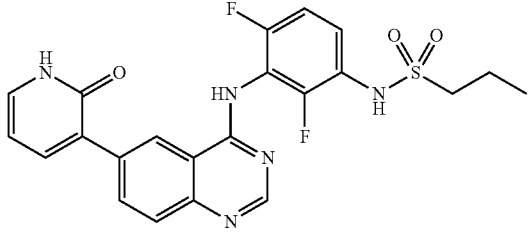 [SMILES: CCCS(=O)(=O)Nc1ccc(F)c(Nc2ncnc3ccc(-c4ccc[nH]c4=O)cc23)c1F]<br>N-(2,4-difluoro-3-(6-(2-oxo-1,2-dihydropyridin-3-yl)quinazolin-4-ylamino)phenyl)propane-1-sulfonamide |
| 27 | 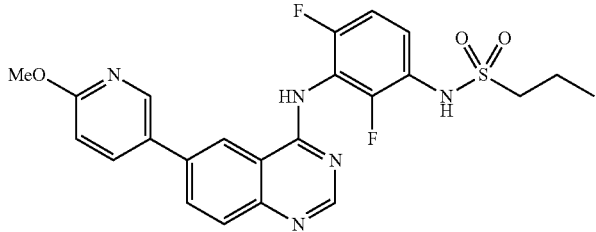 [SMILES: CCCS(=O)(=O)Nc1ccc(F)c(Nc2ncnc3ccc(-c4ccc(OC)nc4)cc23)c1F]<br>N-(2,4-difluoro-3-(6-(6-methoxypyridin-3-yl)quinazolin-4-ylamino)phenyl)propane-1-sulfonamide |

TABLE 1-continued

Quinazoline compounds

| Cpd. ID | Structure |
|---|---|
| 28 | 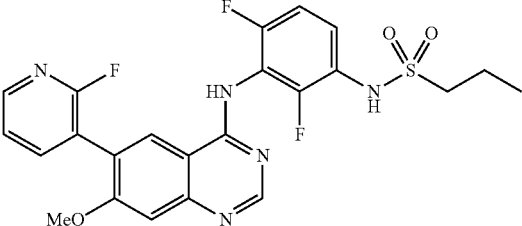 [SMILES: CCCS(=O)(=O)Nc1ccc(F)c(Nc2ncnc3cc(OC)c(-c4cccnc4F)cc23)c1F]<br>N-(2,4-difluoro-3-(6-(2-fluoropyridin-3-yl)-7-methoxyquinazolin-4-ylamino)phenyl)propane-1-sulfonamide |
| 29 | 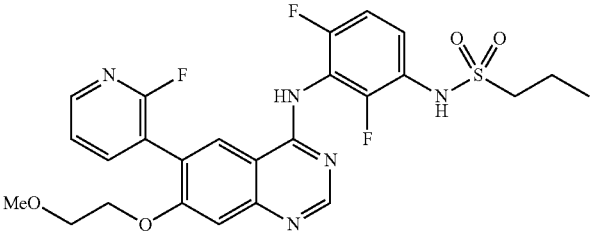 [SMILES: CCCS(=O)(=O)Nc1ccc(F)c(Nc2ncnc3cc(OCCOC)c(-c4cccnc4F)cc23)c1F]<br>N-(2,4-difluoro-3-(6-(2-fluoropyridin-3-yl)-7-(2-methoxyethoxy)quinazolin-4-ylamino)phenyl)propane-1-sulfonamide |
| 30 | 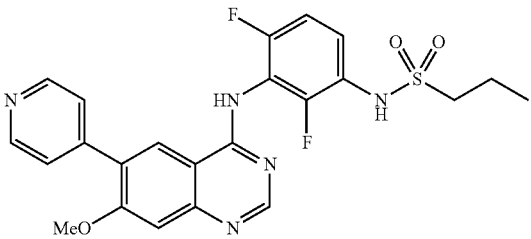 [SMILES: CCCS(=O)(=O)Nc1ccc(F)c(Nc2ncnc3cc(OC)c(-c4ccncc4)cc23)c1F]<br>N-(2,4-difluoro-3-(7-methoxy-6-(pyridin-4-yl)quinazolin-4-ylamino)phenyl)propane-1-sulfonamide |
| 31 | 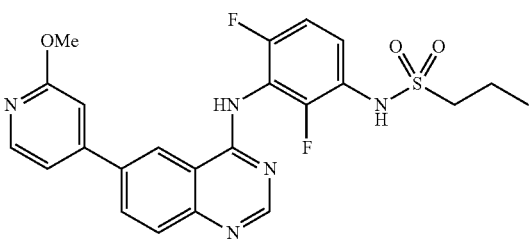 [SMILES: CCCS(=O)(=O)Nc1ccc(F)c(Nc2ncnc3ccc(-c4ccnc(OC)c4)cc23)c1F]<br>N-(2,4-difluoro-3-(6-(2-methoxypyridin-4-yl)quinazolin-4-ylamino)phenyl)propane-1-sulfonamide |

TABLE 1-continued

Quinazoline compounds

| Cpd. ID | Structure |
|---|---|
| 32 | 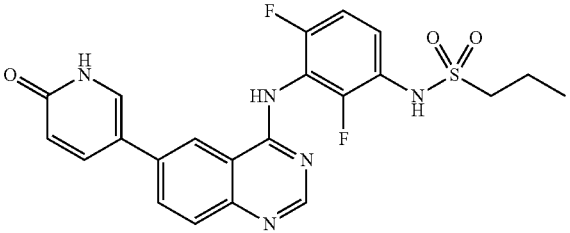 [SMILES: CCCS(=O)(=O)Nc1ccc(F)c(Nc2ncnc3ccc(-c4ccc(=O)[nH]c4)cc23)c1F] N-(2,4-difluoro-3-(6-(6-oxo-1,6-dihydropyridin-3-yl)quinazolin-4-ylamino)phenyl)propane-1-sulfonamide |
| 33 | 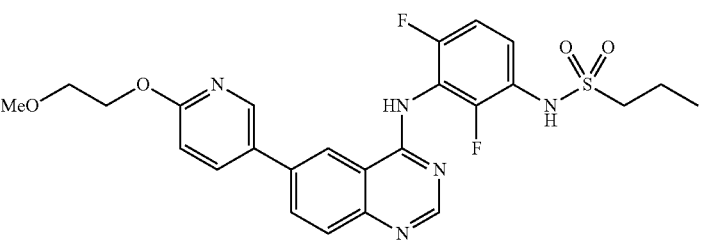 [SMILES: CCCS(=O)(=O)Nc1ccc(F)c(Nc2ncnc3ccc(-c4ccc(OCCOC)nc4)cc23)c1F] N-(2,4-difluoro-3-(6-(6-(2-methoxyethoxy)pyridin-3-yl)quinazolin-4-ylamino)phenyl)propane-1-sulfonamide |
| 34 | 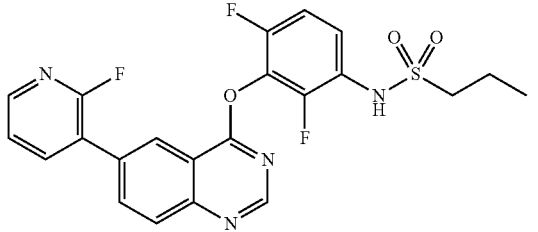 [SMILES: CCCS(=O)(=O)Nc1ccc(F)c(Oc2ncnc3ccc(-c4cccnc4F)cc23)c1F] N-(2,4-difluoro-3-(6-(2-fluoropyridin-3-yl)-quinazolin-4-yloxy)phenyl)propane-1-sulfonamide |
| 35 | 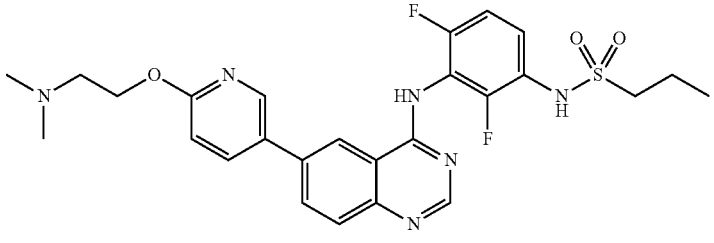 [SMILES: CCCS(=O)(=O)Nc1ccc(F)c(Nc2ncnc3ccc(-c4ccc(OCCN(C)C)nc4)cc23)c1F] N-(3-(6-(6-(2-(dimethylamino)ethoxy)-pyridin-3-yl)quinazolin-4-ylamino)-2,4-difluorophenyl)propane-1-sulfonamide |

TABLE 1-continued

| Quinazoline compounds | |
|---|---|
| Cpd. ID | Structure |
| 36 | 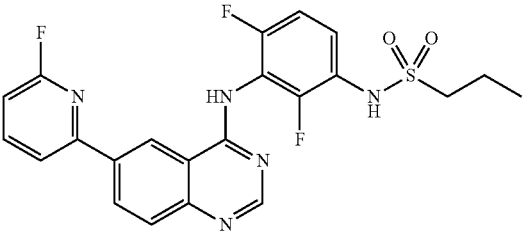 [SMILES: CCCS(=O)(=O)Nc1ccc(F)c(Nc2ncnc3ccc(-c4cccc(F)n4)cc23)c1F]<br>N-(2,4-difluoro-3-(6-(6-fluoropyridin-2-yl)-quinazolin-4-ylamino)phenyl)propane-1-sulfonamide |
| 37 | 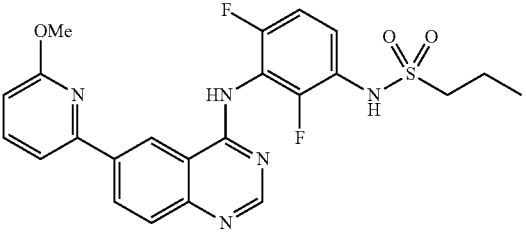 [SMILES: CCCS(=O)(=O)Nc1ccc(F)c(Nc2ncnc3ccc(-c4cccc(OC)n4)cc23)c1F]<br>N-(2,4-difluoro-3-(6-(6-methoxypyridin-2-yl)quinazolin-4-ylamino)phenyl)propane-1-sulfonamide |
| 38 | 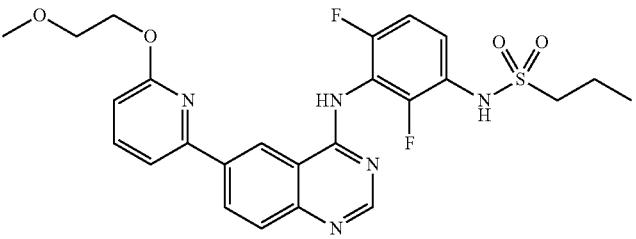 [SMILES: CCCS(=O)(=O)Nc1ccc(F)c(Nc2ncnc3ccc(-c4cccc(OCCOC)n4)cc23)c1F]<br>N-(2,4-difluoro-3-(6-(6-(2-methoxyethoxy)pyridin-2-yl)quinazolin-4-ylamino)phenyl)propane-1-sulfonamide |
| 39 | 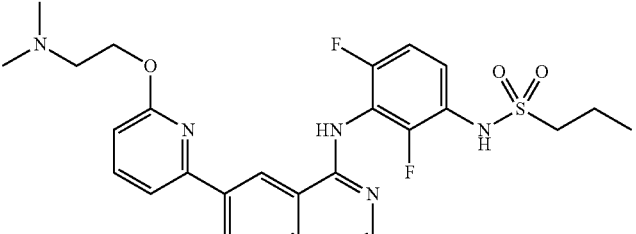<br>N-(3-(6-(6-(2-(dimethylamino)ethoxy)-pyridin-2-yl)quinazolin-4-ylamino)-2,4-difluorophenyl)propane-1-sulfonamide |

TABLE 1-continued

| Quinazoline compounds | |
|---|---|
| Cpd. ID | Structure |

40

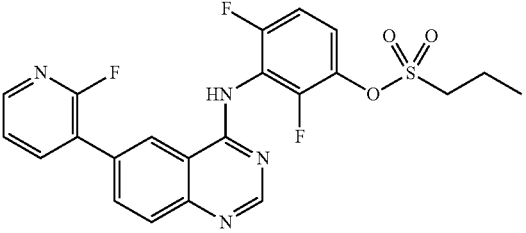 [SMILES: CCCS(=O)(=O)Oc1ccc(F)c(Nc2ncnc3ccc(-c4cccnc4F)cc23)c1F]

2,4-difluoro-3-(6-(2-fluoropyridin-
3-yl)quinazolin-4-ylamino)phenyl
propane-1-sulfonate

41

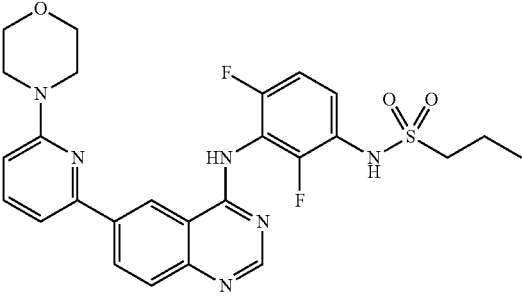 [SMILES: CCCS(=O)(=O)Nc1ccc(F)c(Nc2ncnc3ccc(-c4cccc(N5CCOCC5)n4)cc23)c1F]

N-(2,4-difluoro-3-(6-(6-morpholinopyridin-
2-yl)quinazolin-4-ylamino)phenyl)
propane-1-sulfonamide

42

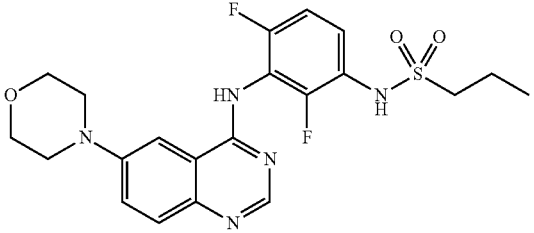 [SMILES: CCCS(=O)(=O)Nc1ccc(F)c(Nc2ncnc3ccc(N4CCOCC4)cc23)c1F]

N-(2,4-difluoro-3-(6-
morpholinoquinazolin-4-ylamino)phenyl)
propane-1-sulfonamide

43

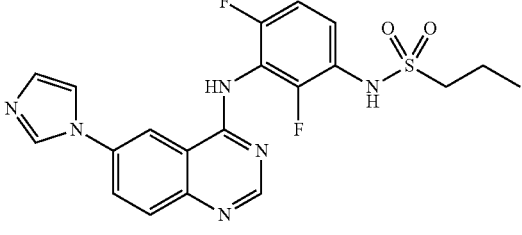

N-(3-(6-(1H-imidazol-1-yl)quinazolin-
4-ylamino)-2,4-difluorophenyl)
propane-1-sulfonamide TABLE 1-continued Quinazoline compounds

| Cpd. ID | Structure |
|---|---|
| 44 | 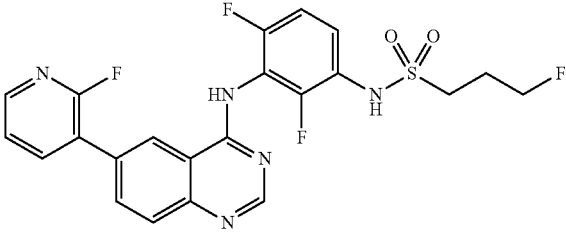 [SMILES: O=S(=O)(CCCF)Nc1ccc(F)c(Nc2ncnc3ccc(-c4cccnc4F)cc23)c1F]<br>N-(2,4-difluoro-3-(6-(2-fluoropyridin-3-yl)quinazolin-4-ylamino)phenyl)-3-fluoropropane-1-sulfonamide |
| 45 | 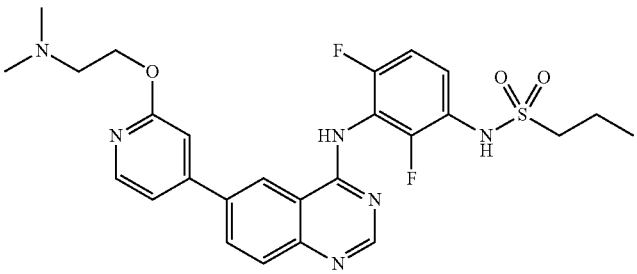 [SMILES: CCCS(=O)(=O)Nc1ccc(F)c(Nc2ncnc3ccc(-c4ccnc(OCCN(C)C)c4)cc23)c1F]<br>N-(3-(6-(2-(2-(dimethylamino)ethoxy)-pyridin-4-yl)quinazolin-4-ylamino)-2,4-difluorophenyl)propane-1-sulfonamide |
| 46 | 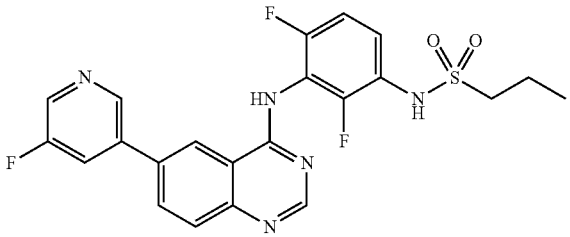 [SMILES: CCCS(=O)(=O)Nc1ccc(F)c(Nc2ncnc3ccc(-c4cncc(F)c4)cc23)c1F]<br>N-(2,4-difluoro-3-(6-(5-fluoropyridin-3-yl)quinazolin-4-ylamino)phenyl)propane-1-sulfonamide |
| 47 | 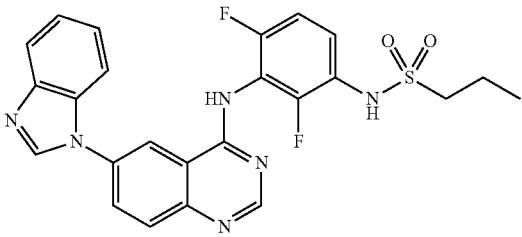 [SMILES: CCCS(=O)(=O)Nc1ccc(F)c(Nc2ncnc3ccc(-n4cnc5ccccc54)cc23)c1F]<br>N-(3-(6-(1H-benzo[d]imidazol-1-yl)-quinazolin-4-ylamino)-2,4-difluorophenyl)propane-1-sulfonamide |

TABLE 1-continued

Quinazoline compounds

| Cpd. ID | Structure |
|---|---|
| 48 | 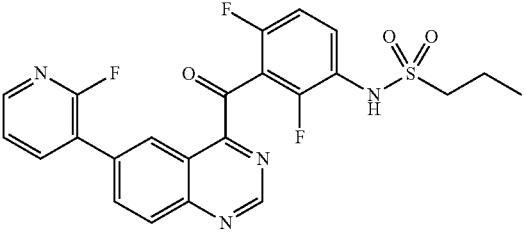 [SMILES: CCCS(=O)(=O)Nc1ccc(F)c(C(=O)c2ncnc3ccc(-c4cccnc4F)cc23)c1F]<br>N-(2,4-difluoro-3-(6-(2-fluoropyridin-3-yl)quinazoline-4-carbonyl)phenyl)propane-1-sulfonamide |
| 49 | 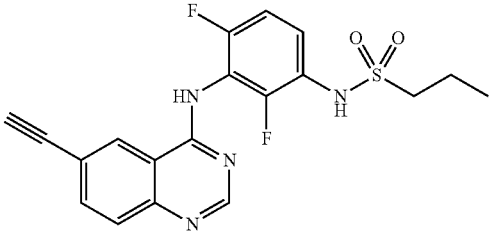 [SMILES: C#Cc1ccc2ncnc(Nc3c(F)ccc(NS(=O)(=O)CCC)c3F)c2c1]<br>N-(3-(6-ethynylquinazolin-4-ylamino)-2,4-difluorophenyl)propane-1-sulfonamide |
| 50 | 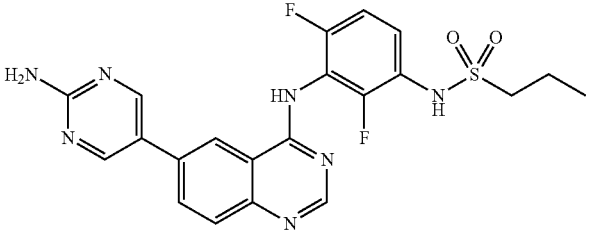 [SMILES: CCCS(=O)(=O)Nc1ccc(F)c(Nc2ncnc3ccc(-c4cnc(N)nc4)cc23)c1F]<br>N-(3-(6-(2-aminopyrimidin-5-yl)quinazolin-4-ylamino)-2,4-difluorophenyl)propane-1-sulfonamide |
| 51 | 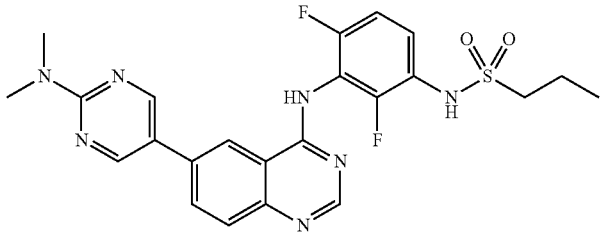 [SMILES: CCCS(=O)(=O)Nc1ccc(F)c(Nc2ncnc3ccc(-c4cnc(N(C)C)nc4)cc23)c1F]<br>N-(3-(6-(2-(dimethylamino)pyrimidin-5-yl)quinazolin-4-ylamino)-2,4-difluorophenyl)propane-1-sulfonamide |

TABLE 1-continued

Quinazoline compounds

| Cpd. ID | Structure |
|---|---|
| 52 | 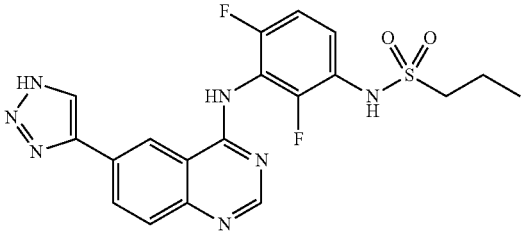 [SMILES: CCCS(=O)(=O)Nc1ccc(F)c(Nc2ncnc3ccc(-c4c[nH]nn4)cc23)c1F]  N-(3-(6-(1H-1,2,3-triazol-4-yl)quinazolin-4-ylamino)-2,4-difluorophenyl)propane-1-sulfonamide |
| 53 | 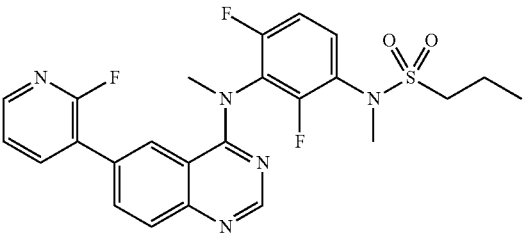 [SMILES: CCCS(=O)(=O)N(C)c1ccc(F)c(N(C)c2ncnc3ccc(-c4cccnc4F)cc23)c1F]  N-(2,4-difluoro-3-((6-(2-fluoropyridin-3-yl)-quinazolin-4-yl)(methyl)amino)phenyl)-N-methylpropane-1-sulfonamide |
| 54 | 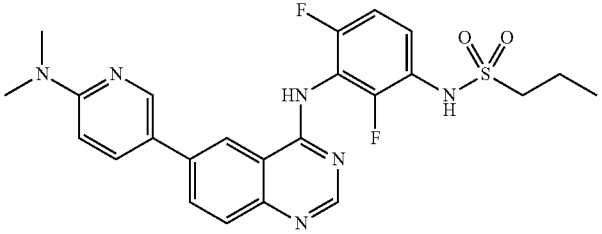 [SMILES: CCCS(=O)(=O)Nc1ccc(F)c(Nc2ncnc3ccc(-c4ccc(N(C)C)nc4)cc23)c1F]  N-(3-(6-(6-(dimethylamino)pyridin-3-yl)quinazolin-4-ylamino)-2,4-difluorophenyl)propane-1-sulfonamide |
| 55 | 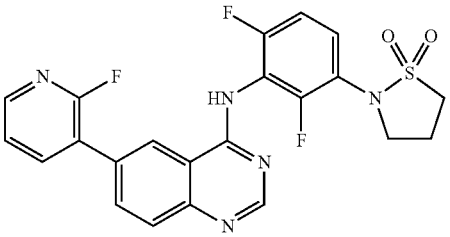 [SMILES: O=S1(=O)CCCN1c1ccc(F)c(Nc2ncnc3ccc(-c4cccnc4F)cc23)c1F] |
| 56 | 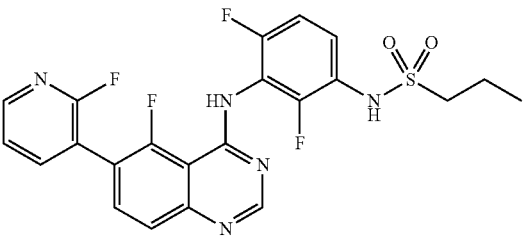  N-(2,4-difluoro-3-(5-fluoro-6-(2-fluoropyridin-3-yl)quinazolin-4-ylamino)phenyl)propane-1-sulfonamide |

TABLE 1-continued

Quinazoline compounds

| Cpd. ID | Structure |
|---|---|
| 57 | 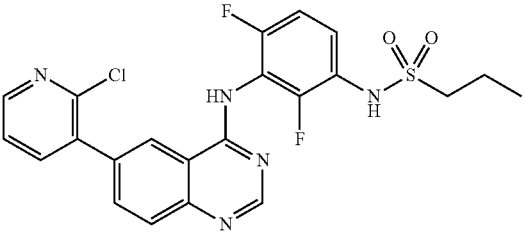<br>N-(3-(6-(2-chloropyridin-3-yl)-quinazolin-4-ylamino)-2,4-difluorophenyl)propane-1-sulfonamide |
| 58 | 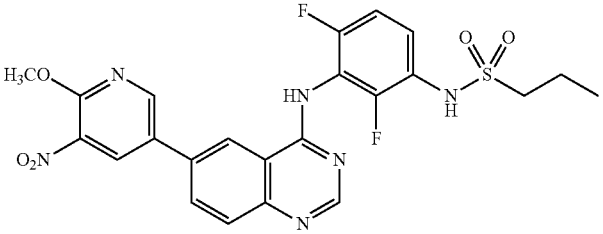 [SMILES: CCCS(=O)(=O)Nc1ccc(F)c(Nc2ncnc3ccc(-c4cnc(OC)c([N+](=O)[O-])c4)cc23)c1F]<br>N-(2,4-difluoro-3-(6-(6-methoxy-5-nitropyridin-3-yl)quinazolin-4-ylamino)phenyl)propane-1-sulfonamide |
| 59 | 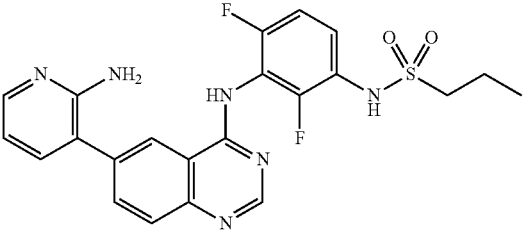 [SMILES: CCCS(=O)(=O)Nc1ccc(F)c(Nc2ncnc3ccc(-c4cccnc4N)cc23)c1F]<br>N-(3-(6-(3-aminophenyl)quinazolin-4-ylamino)-2,4-difluorophenyl)propane-1-sulfonamide |
| 60 | 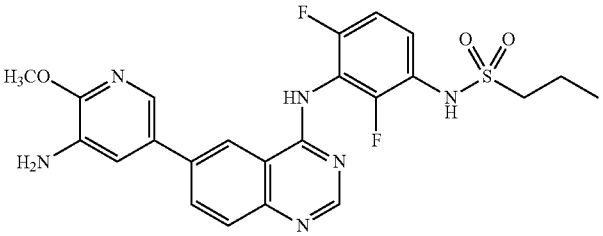<br>N-(3-(6-(5-amino-6-methoxypyridin-3-yl)quinazolin-4-ylamino)-2,4-difluorophenyl)propane-1-sulfonamide |
| 61 | 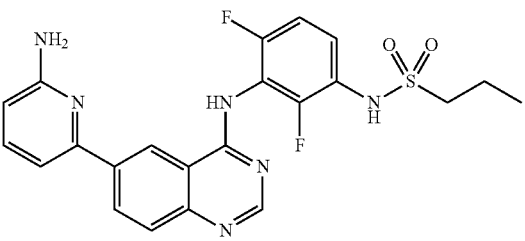 [SMILES: CCCS(=O)(=O)Nc1ccc(F)c(Nc2ncnc3ccc(-c4cccc(N)n4)cc23)c1F]<br>N-(3-(6-(6-aminopyridin-2-yl)quinazolin-4-ylamino)-2,4-difluorophenyl)propane-1-sulfonamide |

TABLE 1-continued

Quinazoline compounds

| Cpd. ID | Structure |
|---|---|
| 62 | 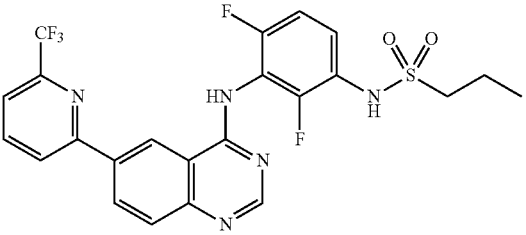 [SMILES: CCCS(=O)(=O)Nc1ccc(F)c(Nc2ncnc3ccc(-c4cccc(C(F)(F)F)n4)cc23)c1F]<br>N-(2,4-difluoro-3-(6-(6-(trifluoromethyl)pyridin-2-yl)quinazolin-4-ylamino)phenyl)propane-1-sulfonamide |
| 63 | 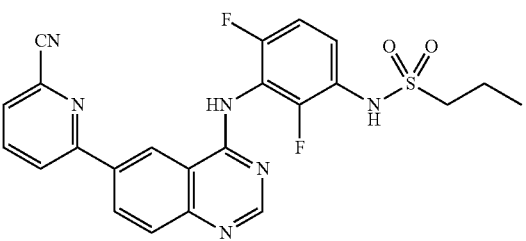 [SMILES: CCCS(=O)(=O)Nc1ccc(F)c(Nc2ncnc3ccc(-c4cccc(C#N)n4)cc23)c1F]<br>N-(3-(6-(6-cyanopyridin-2-yl)quinazolin-4-ylamino)-2,4-difluorophenyl)propane-1-sulfonamide |
| 64 | 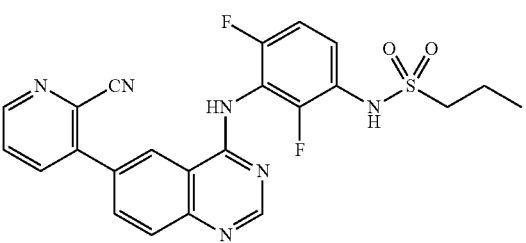 [SMILES: CCCS(=O)(=O)Nc1ccc(F)c(Nc2ncnc3ccc(-c4cccnc4C#N)cc23)c1F]<br>N-(3-(6-(2-cyanopyridin-3-yl)quinazolin-4-ylamino)-2,4-difluorophenyl)propane-1-sulfonamide |
| 65 | 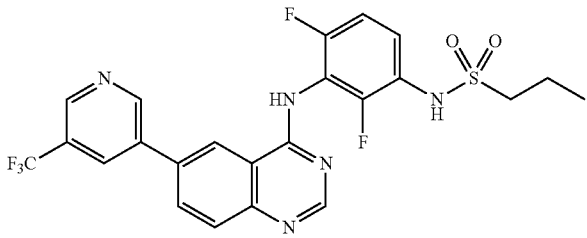 [SMILES: CCCS(=O)(=O)Nc1ccc(F)c(Nc2ncnc3ccc(-c4cncc(C(F)(F)F)c4)cc23)c1F]<br>N-(2,4-difluoro-3-(6-(5-(trifluoromethyl)pyridin-3-yl)quinazolin-4-ylamino)phenyl)propane-1-sulfonamide |
| 66 | 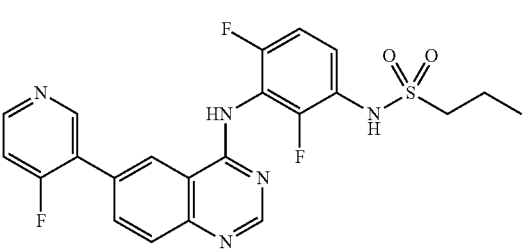 [SMILES: CCCS(=O)(=O)Nc1ccc(F)c(Nc2ncnc3ccc(-c4cnccc4F)cc23)c1F]<br>N-(2,4-difluoro-3-(6-(4-fluoropyridin-3-yl)quinazolin-4-ylamino)phenyl)propane-1-sulfonamide |

TABLE 1-continued

Quinazoline compounds

| Cpd. ID | Structure |
|---|---|
| 67 | 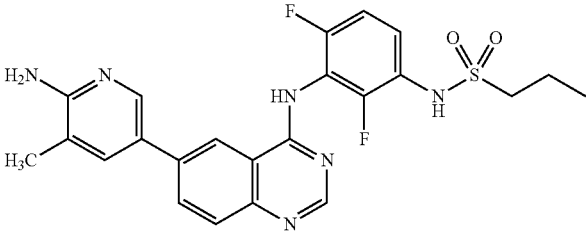 [SMILES: CCCS(=O)(=O)Nc1ccc(F)c(Nc2ncnc3ccc(-c4cnc(N)c(C)c4)cc23)c1F]<br>N-(3-(6-(6-amino-5-methylpyridin-3-yl)quinazolin-4-ylamino)-<br>2,4-difluorophenyl)propane-1-sulfonamide |

TABLE 2 calculated mass and observed ESI-MS data

| Cpd. ID | Calculated Mass | Observed ESI-MS |
|---|---|---|
| 1 | 473.11 | 474.1 (M + H)+ |
| 2 | 540.18 | 541.2 (M + H)+ |
| 3 | 473.11 | 474.1 (M + H)+ |
| 4 | 444.12 | 445.3 (M + H)+ |
| 5 | 455.12 | 456.2 (M + H)+ |
| 6 | 455.12 | 456.1 (M + H)+ |
| 7 | 491.10 | 492.1 (M + H)+ |
| 8 | 602.19 | 603.3 (M + H)+ |
| 9 | 489.08, 491.08 | 490.1, 492.2 (M + H)+ |
| 10 | 445.08 | 446.2 (M + H)+ |
| 11 | 473.11 | 474.3 (M + H)+ |
| 12 | 455.12 | 456.2 (M + H)+ |
| 13 | 472.12 | 473.2 (M + H)+ |
| 14 | 454.13 | 455.2 (M + H)+ |
| 15 | 473.11 | 474.3 (M + H)+ |
| 16 | 473.11 | 474.2 (M + H)+ |
| 17 | 455.12 | 456.1 (M + H)+ |
| 18 | 487.13 | 488.1 (M + H)+ |
| 19 | 459.10 | 460.0 (M + H)+ |
| 20 | 473.11 | 474.1 (M + H)+ |
| 21 | 507.10 | 508.1 (M + H)+ |
| 22 | 541.21 | 542.0 (M + H)+ |
| 23 | 485.13 | 485.9 (M + H)+ |
| 24 | 473.11 | 474.1 (M + H)+ |
| 25 | 472.12 | 473.2 (M + H)+ |
| 26 | 471.12 | 472.3 (M + H)+ |
| 27 | 485.13 | 486.0 (M + H)+ |
| 28 | 503.12 | 504.5 (M + H)+ |
| 29 | 547.15 | 548.2 (M + H)+ |
| 30 | 485.13 | 486.0 (M + H)+ |
| 31 | 485.13 | 486.0 (M + H)+ |
| 32 | 471.12 | 472.2 (M + H)+ |
| 33 | 529.16 | 530.5 (M + H)+ |
| 34 | 474.10 | 475.20 (M + H)+ |
| 35 | 542.19 | 543.3 (M + H)+ |
| 36 | 473.11 | 474.1 (M + H)+ |
| 37 | 485.13 | 486.2 (M + H)+ |
| 38 | 529.10 | 530.5 (M + H)+ |
| 39 | 542.19 | 543.3 (M + H)+ |
| 40 | 474.10 | 475.2 (M + H)+ |
| 41 | 540.18 | 541.1 (M + H)+ |
| 42 | 463.15 | 464.1 (M + H)+ |
| 43 | 444.12 | 445.4 (M + H)+ |
| 44 | 491.10 | 492.10 (M + H)+ |
| 45 | 542.19 | 543.4 (M + H)+ |
| 46 | 473.11 | 474.1 (M + H)+ |
| 47 | 494.13 | 495.4 (M + H)+ |
| 48 | 486.10 | 487.0 (M + H)+ |
| 49 | 402.10 | 402.8 (M + H)+ |
| 50 | 471.13 | 472.1 (M + H)+ |
| 51 | 499.16 | 500.3 (M + H)+ |
| 52 | 445.11 | 446.2 (M + H)+ |
| 53 | 501.14 | 502.4 (M + H)+ |
| 54 | 498.16 | 499.4 (M + H)+ |
| 55 | 471.10 | 472.2 (M + H)+ |
| 56 | 491.10 | 492.1 (M + H)+ |
| 57 | 489.93 | 490.1, 491.5 (M + H)+ |
| 58 | 530.50 | 531.5 (M + H)+ |
| 59 | 470.50 | 471.0 (M + H)+ |
| 60 | 500.52 | 501.2 (M + H)+ |
| 61 | 470.50 | 471.0 (M + H)+ |
| 62 | 523.48 | 524.1 (M + H)+ |
| 63 | 480.49 | 480.9 (M + H)+ |
| 64 | 480.49 | 480.9 (M + H)+ |
| 65 | 523.48 | 524.1 (M + H)+ |
| 66 | 473.47 | 474.1 (M + H)+ |
| 67 | 484.52 | 485.0 (M + H)+ |

Biological Activity

Biological Activity

Various compounds of formula I were tested for their abilities to inhibit a variety of protein kinases. Brief descriptions of different assays are described below.

1. B-Raf Kinase Assay

Inhibition of kinase activity by a test compound disclosed herein was estimated by quantifying the amount of [$^{33}$P] incorporation of a substrate in the presence of the test compound. Standard assay conditions were 5 ng of recombinant B-Raf kinase (Upstate Biotechnology) with 500 ng MEK1 (K97R) in assay buffer (8 μM ATP, 0.5 μCi [$^{33}$P]ATP (specific activity 3000 Ci/mmol, PerkinElmer), 50 mM Tris/HCl (pH7.5), and 1 mM EGTA, 1 mM Na$_3$VO$_4$, 1% 2-mercaptoethanol, 0.1% Brij 35, and 0.2 mg/ml BSA) in a final volume of 25 μL. Reactions were incubated at 30° C. for 30 min and stopped by adding 3% phosphoric acid, harvested onto a 96-well GF/B UniFilter (PerkinElmer) using a unifilter harvester (PerkinElmer), and counted with a TopCount microplate scintillation counter (PerkinElmer). The IC$_{50}$ values of inhibitors were determined after carrying out assays at 3-fold serially diluted concentrations of each compound in duplication. The results were analyzed using linear regression software (GraphPad Prism 4; GraphPad Software Inc.).

Inhibition activities of the compounds listed in Table 1 are summarized in Table 2. IC$_{50}$ value is defined as the concentration of the test compound which achieves a half-maximal inhibition of the kinase activity. + represents that the concentration is 10,000~1,000 nM; ++ represents that the concentration is 1,000-300 nM; and +++ represents that the concentration is less than 300 nM.

TABLE 3

| Cpd. ID | IC$_{50}$ against B-Raf kinase |
|---|---|
| 1 | +++ |
| 2 | +++ |
| 3 | +++ |
| 4 | +++ |
| 5 | >10 μM |
| 6 | + |
| 7 | +++ |
| 8 | +++ |
| 9 | + |
| 10 | + |
| 11 | >10 μM |
| 12 | +++ |
| 13 | +++ |
| 14 | +++ |
| 15 | +++ |
| 16 | >10 μM |
| 17 | + |
| 18 | +++ |
| 19 | + |
| 20 | + |
| 21 | +++ |
| 22 | >10 μM |
| 23 | + |
| 24 | +++ |
| 25 | +++ |
| 26 | + |
| 27 | ++ |
| 28 | +++ |
| 29 | +++ |
| 30 | + |
| 31 | +++ |
| 32 | +++ |
| 33 | ++ |
| 34 | ++ |
| 35 | +++ |
| 36 | +++ |
| 37 | +++ |
| 38 | +++ |
| 39 | +++ |
| 40 | >10 μM |
| 41 | ++ |
| 42 | + |
| 43 | + |
| 44 | +++ |
| 45 | +++ |
| 46 | +++ |
| 47 | >10 μM |
| 48 | +++ |
| 49 | + |
| 50 | +++ |
| 51 | ++ |
| 52 | >10 μM |
| 53 | ++ |
| 54 | ++ |
| 55 | >10 μM |
| 56 | ++ |
| 57 | +++ |
| 58 | +++ |
| 59 | ++ |
| 60 | ++ |
| 61 | ++ |
| 62 | +++ |
| 63 | +++ |
| 64 | ++ |
| 65 | ++ |
| 66 | +++ |
| 67 | ++ |

2. B-Raf(V600E) Kinase Assay

Inhibition of kinase activity by a test compound disclosed herein was estimated by quantifying the amount of [$^{33}$P] incorporation of a substrate in the presence of the test compound. Standard assay conditions were 5 ng of recombinant B-Raf(V600E) kinase (Upstate Biotechnology) with 500 ng MEK1 (K97R) in assay buffer (8 μM ATP, 0.5 μCi [$^{33}$P] ATP (specific activity 3000 Ci/mmol, PerkinElmer), 50 mM Tris/HCl (pH7.5), and 1 mM EGTA, 1 mM Na$_3$VO$_4$, 1% 2-mercaptoethanol, 0.1% Brij 35, and 0.2 mg/ml BSA), and the test compound (diluted with 4% DMSO) or DMSO alone (as a control) in a final volume of 25 μL. Reactions were incubated at 30° C. for 30 min and stopped by adding 3% phosphoric acid, harvested onto a 96-well GF/B UniFilter (PerkinElmer) using a unifilter harvester (PerkinElmer), and counted with a TopCount microplate scintillation counter (PerkinElmer). The IC$_{50}$ values of inhibitors were determined after carrying out assays at 3-fold serially diluted concentrations of each compound in duplication. The results were analyzed using linear regression software (GraphPad Prism 4; GraphPad Software Inc.).

Inhibition activities of the selected compounds listed in Table 1 are summarized in Table 4. IC$_{50}$ value is defined as the concentration of the test compound which achieves a half-maximal inhibition of the kinase activity. + represents that the concentration is 10,000~1,000 nM; ++ represents that the concentration is 1,000-300 nM; and +++ represents that the concentration is less than 300 nM.

TABLE 4

| Cpd. ID | IC$_{50}$ against B-Raf(V600E) kinase |
|---|---|
| 1 | +++ |
| 2 | +++ |
| 3 | +++ |
| 4 | +++ |
| 7 | +++ |
| 8 | +++ |
| 9 | + |
| 12 | +++ |
| 13 | +++ |
| 14 | +++ |
| 15 | +++ |
| 18 | +++ |
| 21 | +++ |
| 24 | +++ |
| 25 | +++ |
| 27 | +++ |
| 28 | +++ |
| 29 | +++ |
| 31 | +++ |
| 32 | +++ |
| 35 | +++ |
| 36 | +++ |
| 37 | +++ |
| 38 | +++ |
| 39 | +++ |
| 44 | +++ |
| 45 | +++ |
| 46 | +++ |
| 48 | +++ |
| 50 | ++ |
| 51 | ++ |
| 54 | ++ |
| 57 | +++ |
| 58 | +++ |
| 62 | +++ |
| 63 | +++ |
| 66 | +++ |

3. C-Raf Kinase Assays

Inhibition of kinase activity by a test compound disclosed herein was estimated by quantifying the amount of [$^{33}$P] incorporation of a substrate in the presence of the test compound. Standard assay conditions were 2 ng of recombinant C-Raf kinase (Upstate Biotechnology) with 500 ng MEK1 (K97R) in assay buffer (8 µM ATP, 0.5 µCi [$^{33}$P] ATP (specific activity 3000 Ci/mmol, PerkinElmer), 50 mM Tris/HCl (pH7.5), and 1 mM EGTA, 1 mM Na$_3$VO$_4$, 1% 2-mercaptoethanol, 0.1% Brij 35, and 0.2 mg/ml BSA), and the test compound (diluted with 4% DMSO) or DMSO alone (as a control) in a final volume of 25 µL. Reactions were incubated at 30° C. for 30 min and stopped by adding 3% phosphoric acid, harvested onto a 96-well GF/B UniFilter (PerkinElmer) using a unifilter harvester (PerkinElmer), and counted with a TopCount microplate scintillation counter (PerkinElmer). The IC$_{50}$ values of inhibitors were determined after carrying out assays at 3-fold serially diluted concentrations of each compound in duplication. The results were analyzed using linear regression software (GraphPad Prism 4; GraphPad Software Inc.).

Inhibition activities of the selected compounds with IC$_{50}$ value against B-Raf kinase <300 nM are summarized in Table 5. IC$_{50}$ value is defined as the concentration of the test compound which achieves a half-maximal inhibition of the kinase activity. + represents that the concentration is 10,000~1,000 nM; ++ represents that the concentration is 1,000-300 nM; and +++ represents that the concentration is less than 300 nM.

TABLE 5

| Cpd. ID | IC$_{50}$ against C-Raf kinase |
|---|---|
| 1 | +++ |
| 2 | +++ |
| 3 | +++ |
| 4 | +++ |
| 7 | +++ |
| 8 | ++ |
| 9 | + |
| 12 | +++ |
| 13 | +++ |
| 14 | +++ |
| 15 | +++ |
| 18 | +++ |
| 21 | +++ |
| 24 | ++ |
| 25 | +++ |
| 27 | +++ |
| 28 | +++ |
| 29 | +++ |
| 31 | +++ |
| 32 | ++ |
| 35 | + |
| 36 | ++ |
| 37 | ++ |
| 38 | ++ |
| 39 | + |
| 44 | +++ |
| 45 | + |
| 46 | +++ |
| 48 | +++ |
| 50 | ++ |
| 51 | + |
| 54 | ++ |
| 57 | +++ |
| 58 | +++ |
| 62 | +++ |
| 63 | +++ |
| 66 | +++ |

4. VEGFR2 and EGFR Kinase Assays

Quinazoline is a well-known backbone structure for the development of ATP competitive kinase inhibitors, in particular against EGFR and VEGFR2 kinases. However, the novel quinazoline derivatives of this invention unexpectedly exhibit selective inhibition activities against Raf kinases, instead of VEGFR2 or EGFR kinase, as shown below.

The follow shows results of inhibitions of VEGFR2, EGFR, or Raf kinases. The inhibitory activity against VEGFR2 or EGFR was determined by radiometric kinase assay. The experimental condition for VEGFR2 kinase assay was 6.25 ng of recombinant VEGFR2 kinase (VEGFR2 kinase domain alone, Millipore), 5 µg of substrate Poly(Glu-Tyr) (4:1, Sigma), kinase reaction buffer (20 mM MOPS pH 7.0, 1 mM EDTA, 5% glycerol, 0.01% Brij-35, 0.1% β-mercaptoethanol, 1 mg/mL BSA, 100 µM ATP, and 0.1 µCi per well [$^{33}$P] ATP (specific activity 3000 Ci/mmol, PerkinElmer)), and the test compound (diluted with 4% DMSO) or DMSO alone (as a control) in a final volume of 25 µL. Reactions were incubated at 30° C. for 30 min and stopped by adding 3% phosphoric acid, harvested onto a 96-well GF/B UniFilter (PerkinElmer) using a unifilter harvester (PerkinElmer), and counted with a TopCount microplate scintillation counter (PerkinElmer).

The experimental condition for EGFR kinase assay was 25 ng of EGFR kinase (EGFR kinase domain alone, Millipore), 3 µg of the substrate poly(Glu-Tyr), (Sigma), kinase reaction buffer (10 mM MOPS pH 7.0, 0.3 mM EDTA, 0.5% glycerol, 0.001% Brij-35, 10 mM MnCl$_2$, 0.1 mg/ml BSA, 100 µM ATP, and 0.1 µCi per well [$^{33}$P]ATP (specific activity 3000 Ci/mmol, PerkinElmer)), and the test compound (diluted with 4% DMSO) or DMSO (as a control) in a final volume of 25 µL. Reactions were incubated at 30° C. for 30 min and stopped by adding 3% phosphoric acid, harvested onto a 96-well GF/B UniFilter (PerkinElmer) using a unifilter harvester (PerkinElmer), and counted with a TopCount microplate scintillation counter (PerkinElmer).

Results of inhibition activity against VEGFR2 and EGFR kinases by the selected compounds, which have IC$_{50}$ values on B-Raf kinase <300 nM, are summarized in Table 6. IC$_{50}$ value is defined as the concentration of the test compound which achieves a half-maximal inhibition of the kinase activity. + represents that the concentration is 3,000~1,000 nM; ++ represents that the concentration is 1,000-300 nM; and +++ represents that the concentration is less than 300 nM.

TABLE 6

| | Inhibition activity, IC$_{50}$ | |
|---|---|---|
| Cpd. ID | VEGFR2 | EGFR |
| 1 | >3 µM | >3 µM |
| 2 | >3 µM | + |
| 3 | >3 µM | >3 µM |
| 4 | >3 µM | ++ |
| 7 | >3 µM | >3 µM |
| 8 | >3 µM | >3 µM |
| 12 | >3 µM | ++ |
| 13 | >3 µM | >3 µM |
| 14 | >3 µM | + |
| 15 | >3 µM | + |
| 18 | >3 µM | >3 µM |
| 21 | >3 µM | + |
| 24 | >3 µM | + |
| 25 | >3 µM | >3 µM |
| 27 | >3 µM | + |
| 28 | >3 µM | ++ |

TABLE 6-continued

| Cpd. ID | Inhibition activity, IC$_{50}$ VEGFR2 | EGFR |
|---|---|---|
| 29 | >3 µM | ++ |
| 31 | >3 µM | ++ |
| 32 | >3 µM | >3 µM |
| 35 | >3 µM | ++ |
| 36 | >3 µM | + |
| 37 | >3 µM | ++ |
| 38 | >3 µM | + |
| 39 | >3 µM | >3 µM |
| 44 | >3 µM | >3 µM |
| 45 | >3 µM | >3 µM |
| 46 | >3 µM | >3 µM |
| 48 | >3 µM | >3 µM |
| 50 | >3 µM | >3 µM |
| 57 | >3 µM | >3 µM |
| 58 | >3 µM | >3 µM |
| 62 | >3 µM | ++ |
| 63 | >3 µM | ++ |
| 66 | >3 µM | >3 µM |

As shown in Table 6, the novel quinazoline derivatives of this invention unexpectedly exhibit selectivity in the inhibition of Raf kinases, as compared to inhibition of VEGFR2 or EGFR kinase. These compounds all exhibit IC$_{50}$ values less than 300 nM against Raf kinases. However, they are much weaker inhibitors of VEGFR2 or EGFR kineses, as evidenced by high IC$_{50}$ values (e.g., often >3 µM). The unexpected selectivity of these novel quinazoline compounds indicate that they can be used in therapies that require selective control of the Raf kinases activities.

5. Cell Proliferation Assay

As noted above, compounds of the invention may be used to treat protein kinase-related diseases or disorders. The protein kinase related disease may be cancer, diabetes, a renal disease, von Hip-pel-Lindau disease, fibrosis, osteoarthritis, an autoimmune disease, or a blood vessel proliferative disorder. The cancer may be lung cancer, colon cancer, colorectal cancer, breast cancer, prostate cancer, liver cancer, pancreatic cancer, bladder cancer, gastric cancer, renal cancer, salivary gland cancer, ovarian cancer, uterine body cancer, cervical cancer, oral cancer, skin cancer, brain cancer, lymphoma, or leukemia.

The anti-proliferative activities of compounds of formula (I) against B-Raf(V600E) mutant human cancer cell lines, A375 melanoma cells and COLO205 colon cancer cells, were measured using the CellTiter™-96 assay kit (Promega) following the manufacturer's instructions. In brief, the cells were maintained in DMEM containing 10% FCS and incubated at 37° C. in 5% CO$_2$ atmosphere. Cells were plated at a density of 2,000 cells/well on a 96-well plate and incubated for 24 h. Then, these cells were treated with different concentrations of the test compounds and incubated for another 72 hours. At the end of the incubation, CellTiter™-96 Aqueous One Solution Reagent (Promega) was added and incubated for another 4.0 hours. Cell viability was determined by measuring absorbance at 490 nm using EMax® microplate reader (Molecular Devices). Data were processed and analyzed using GraphPad Prism. The test compounds that have anti-proliferative activities with IC$_{50}$<2 µM are summarized in Table 7.

TABLE 7

| Cytotoxicity | Compounds |
|---|---|
| IC$_{50}$ < 2 µM for A375 or COLO205 | 1, 2, 3, 7, 8, 12, 13, 14, 15, 18, 21, 24, 25, 27, 28, 29, 31, 32, 35, 36, 37, 38, 39, 44, 45, 46, 50, 57, 58, 62, 63, and 66. |

Data in Table 7 clearly show that compounds of the invention can inhibit cancer cell growth. Therefore, these compounds may be used in the treatment of cancers.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:
1. A compound of formula (I):

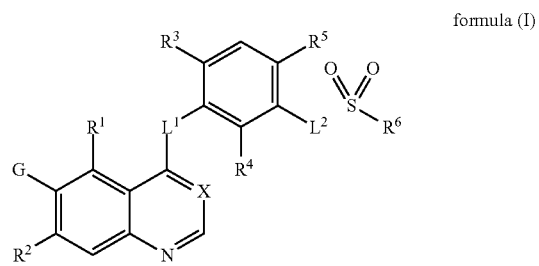

formula (I)

or a stereoisomer, a tautomer, a pharmaceutically acceptable salt thereof,
wherein:
G is a heteroaryl, heterocycle, or alkyne;
X is N or CH;
L$^1$ is selected from the group consisting of —N(R$^7$)—, —O—, —C(S)—, —C(O)—, and —S—, wherein R$^7$ is hydrogen or C$_1$-C$_4$ alkyl;
L$^2$ is selected from the group consisting of —N(R$^8$)— and —O—, wherein R$^8$ is hydrogen or C$_1$-C$_4$ alkyl;
R$^1$ and R$^2$ are independently selected from the group consisting of hydrogen, halogen, hydroxyl, amino, cyano, nitro, carboxy, C$_1$-C$_4$ alkoxy, C$_1$-C$_4$ alkoxy C$_1$-C$_4$ alkoxy, N,N—(C$_1$-C$_4$ dialkyl)amino C$_1$-C$_4$ alkoxy, N—(C$_1$-C$_4$ alkyl)amino C$_1$-C$_4$ alkoxy, C$_1$-C$_4$ alkanoyl, C$_1$-C$_4$ alkanoyloxy, N—(C$_1$-C$_4$ alkyl)amino, N,N—(C$_1$-C$_4$ dialkyl)amino, C$_1$-C$_4$ alkanoyl amino, and heterocyclyl, wherein C$_1$-C$_4$ alkyl is optionally substituted with one or more substituents selected from the group consisting of fluorine and chlorine;
R$^3$, R$^4$ and R$^5$ are independently selected from the group consisting of hydrogen, fluorine, and chlorine; and
R$^6$ is selected from the group consisting of C$_1$-C$_4$ alkyl and aryl, wherein C$_1$-C$_4$ alkyl and aryl are independently optionally substituted with one or more substituents selected from the group consisting of halogen, hydroxyl, amino, cyano, and nitro; alternatively, when L$^2$ is —N(R$^8$)—, R$^6$ and R$^8$, together with the atoms to which they are attached, form a 5-6 membered cyclyl or heterocyclyl.

2. The compound of claim 1, wherein the G is selected from:

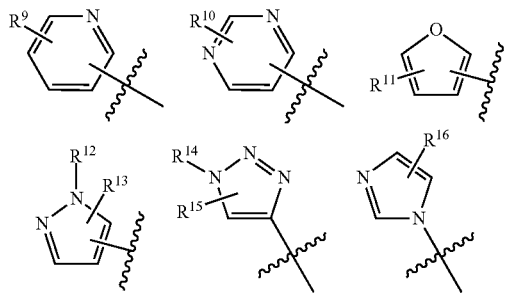

wherein

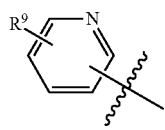

represents a pyridine ring optionally substituted with one or more R$^9$, wherein

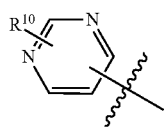

represents a pyrimidine optionally substituted with one or more R$^{10}$, wherein

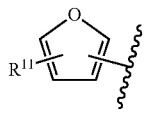

represents a furan optionally substituted with one or more R$^{11}$, wherein

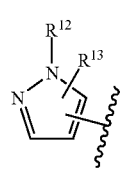

represents a pyrazole optionally, independently substituted with R$^{12}$ and one or more R$^{13}$, wherein

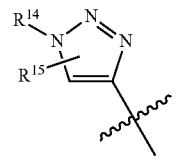

represents a triazole optionally, independently substituted with R$^{14}$ and one or more R$^{15}$, wherein

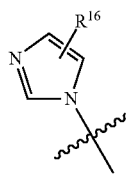

represents an imidazole optionally substituted with one or more R$^{16}$; and wherein R$^9$ is independently selected from the group consisting of hydrogen, halogen, hydroxyl, amino, C$_1$-C$_4$ alkoxy, methoxy C$_1$-C$_4$ alkoxy, C$_1$-C$_4$ dialkylamino C$_1$-C$_4$ alkoxy, C$_1$-C$_4$ dialkylamino, and heterocyclyl; R$^{10}$ is independently hydrogen, hydroxyl, amino, or C$_1$-C$_4$ dialkylamino; R$^{11}$, R$^{13}$, R$^{15}$ and R$^{16}$ are independently hydrogen, halogen, or C$_1$-C$_4$ alkyl; R$^{12}$, R$^{14}$ are independently hydrogen, C$_1$-C$_4$ alkyl, or C$_1$-C$_4$ alkanoyl.

3. The compound of claim 1, wherein the G is selected from:

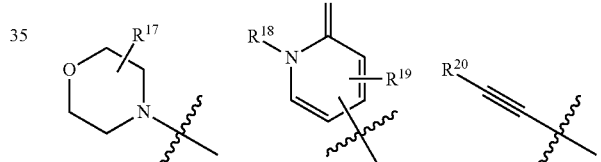

wherein

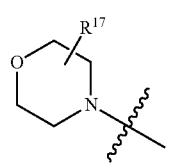

represents a morpholine optionally substituted with one or more R$^{17}$, wherein

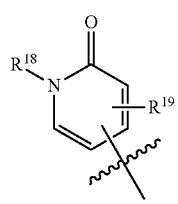

represents a pyridone optionally, independently substituted with R$^{18}$ and one or more R$^{19}$, wherein

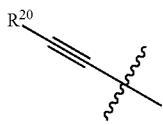

represents an alkyne optionally substituted with $R^{20}$, and wherein $R^{17}$ is independently selected from the group consisting of hydrogen, halogen, hydroxyl, amino, cyano, $C_1$-$C_4$ alkyl, and $C_1$-$C_4$ alkoxy; $R^{18}$ is selected from the group consisting of hydrogen and $C_1$-$C_4$ alkyl; $R^{19}$ is independently selected from the group consisting of hydrogen, halogen, hydroxyl, amino, cyano, $C_1$-$C_4$ alkyl, and $C_1$-$C_4$ alkoxy; $R^{20}$ is selected from the group consisting of hydrogen, $C_1$-$C_4$ alkyl, methoxy $C_1$-$C_4$ alkoxy, and aryl.

4. The compound as claimed in claim 1, wherein $L^2$ is NH.
5. The compound of claim 1, wherein $L^1$ is NH.
6. The compound of claim 1, wherein $R^5$ is hydrogen.
7. The compound of claim 1, wherein $R^3$ and $R^4$ are fluorine.
8. A pharmaceutical composition, comprising a compound claim 1, a salt thereof, a stereoisomer thereof, or a prodrug thereof; and a pharmaceutically acceptable carrier.
9. The compound of claim 1, where the compound is:
N-(2,4-difluoro-3-(6-(2-fluoropyridin-3-yl)quinazolin-4-ylamino)phenyl)propane-1-sulfonamide;
N-(2,4-difluoro-3-(6-(6-morpholinopyridin-3-yl)quinazolin-4-ylamino)phenyl)propane-1-sulfonamide;
N-(2,4-difluoro-3-(6-(6-fluoropyridin-3-yl)quinazolin-4-ylamino)phenyl)propane-1-sulfonamide;
N-(3-(6-(1H-pyrazol-4-yl)quinazolin-4-ylamino)-2,4-difluorophenyl)propane-1-sulfonamide;
N-(2,4-difluoro-3-(6-(pyridin-3-yl)quinazolin-4-ylamino)phenyl)propane-1-sulfonamide;
N-(4-fluoro-3-(6-(2-fluoropyridin-3-yl)quinazolin-4-ylamino)phenyl)propane-1-sulfonamide;
N-(2,4-difluoro-3-(7-fluoro-6-(2-fluoropyridin-3-yl)quinazolin-4-ylamino)phenyl)propane-1-sulfonamide;
N-(2-chloro-4-fluoro-3-(6-(2-fluoropyridin-3-yl)quinazolin-4-ylamino)phenyl)propane-1-sulfonamide;
N-(2,4-difluoro-3-(6-(2-fluoropyridin-3-yl)quinazolin-4-ylamino)phenyl)methanesulfonamide;
N-(2,4-difluoro-5-(6-(2-fluoropyridin-3-yl)quinazolin-4-ylamino)phenyl)propane-1-sulfonamide;
N-(2,4-difluoro-3-(6-(pyridin-4-yl)quinazolin-4-ylamino)phenyl)propane-1-sulfonamide;
N-(2,4-difluoro-3-(6-(2-fluoropyridin-3-yl)quinolin-4-ylamino)phenyl)propane-1-sulfonamide;
N-(2,4-difluoro-3-(6-(pyridin-4-yl)quinolin-4-ylamino)phenyl)propane-1-sulfonamide;
N-(2,4-difluoro-3-(7-fluoro-6-(pyridin-4-yl)quinazolin-4-ylamino)phenyl)propane-1-sulfonamide;
N-(2,6-difluoro-3-(6-(2-fluoropyridin-3-yl)quinazolin-4-ylamino)phenyl)propane-1-sulfonamide;
N-(2,6-difluoro-3-(6-(pyridin-4-yl)quinazolin-4-ylamino)phenyl)propane-1-sulfonamide;
N-(2,4-difluoro-3-(6-(2-fluoropyridin-3-yl)quinazolin-4-ylamino)phenyl)butane-1-sulfonamide;
N-(2,4-difluoro-3-(6-(2-fluoropyridin-3-yl)quinazolin-4-ylamino)phenyl)ethanesulfonamide;
N-(2,4-difluoro-3-(6-(2-fluoropyridin-3-yl)quinazolin-4-ylamino)phenyl)propane-2-sulfonamide;
N-(2,4-difluoro-3-(6-(2-fluoropyridin-3-yl)quinazolin-4-ylamino)phenyl)benzenesulfonamide;
N-(3-(7-(2-(dimethylamino)ethylamino)-6-(pyridin-4-yl)quinazolin-4-ylamino)-2,6-difluorophenyl)propane-1-sulfonamide;
N-(2,4-difluoro-3-(6-(2-methoxypyridin-3-yl)quinolin-4-ylamino)phenyl)propane-1-sulfonamide;
N-(2,4-difluoro-3-(6-(2-fluoropyridin-4-yl)quinazolin-4-ylamino)phenyl)propane-1-sulfonamide;
N-(2,4-difluoro-3-(6-(2-fluoropyridin-4-yl)quinolin-4-ylamino)phenyl)propane-1-sulfonamide;
N-(2,4-difluoro-3-(6-(2-oxo-1,2-dihydropyridin-3-yl)quinazolin-4-ylamino)phenyl)propane-1-sulfonamide;
N-(2,4-difluoro-3-(6-(6-methoxypyridin-3-yl)quinazolin-4-ylamino)phenyl)propane-1-sulfonamide;
N-(2,4-difluoro-3-(6-(2-fluoropyridin-3-yl)-7-methoxyquinazolin-4-ylamino)phenyl)benzenesulfonamide;
N-(2,4-difluoro-3-(6-(2-fluoropyridin-3-yl)-7-(2-methoxyethoxy)quinazolin-4-ylamino)phenyl)propane-1-sulfonamide;
N-(2,4-difluoro-3-(7-methoxy-6-(pyridin-4-yl)quinazolin-4-ylamino)phenyl)propane-1-sulfonamide;
N-(2,4-difluoro-3-(6-(2-methoxypyridin-4-yl)quinazolin-4-ylamino)phenyl)propane-1-sulfonamide;
N-(2,4-difluoro-3-(6-(6-oxo-1,6-dihydropyridin-3-yl)quinazolin-4-ylamino)phenyl)propane-1-sulfonamide;
N-(2,4-difluoro-3-(6-(6-(2-methoxyethoxyl)pyridin-3-yl)quinazolin-4-ylamino)phenyl)propane-1-sulfonamide;
N-(2,4-difluoro-3-(6-(2-fluoropyridin-3-yl)quinazolin-4-yloxy)phenyl)propane-1-sulfonamide;
N-(3-(6-(2-(dimethylamino)ethoxy)pyridin-3-yl)quinazolin-4-ylamino)-2,4-difluorophenyl)propane-1-sulfonamide;
N-(2,4-difluoro-3-(6-(6-fluoropyridin-2-yl)quinazolin-4-ylamino)phenyl)propane-1-sulfonamide;
N-(2,4-difluoro-3-(6-(6-methoxypyridin-2-yl)quinazolin-4-ylamino)phenyl)propane-1-sulfonamide;
N-(2,4-difluoro-3-(6-(6-(2-methoxyethoxy)pyridin-2-yl)quinazolin-4-ylamino)phenyl)propane-1-sulfonamide;
N-(3-(6-(6-(2-(dimethylamino)ethoxy)pyridin-2-yl)quinazolin-4-ylamino)-2,4-difluorophenyl)propane-1-sulfonamide;
N-(2,4-difluoro-3-(6-(2-fluoropyridin-3-yl)quinazolin-4-ylamino)phenyl)propane-1-sulfonate;
N-(2,4-difluoro-3-(6-(6-morpholinopyridin-2-yl)quinazolin-4-ylamino)phenyl)propane-1-sulfonamide;
N-(2,4-difluoro-3-(6-morpholinoquinazolin-4-ylamino)phenyl)propane-1-sulfonamide;
N-(3-(6-(1H-imidazol-1-yl)quinazolin-4-ylamino)-2,4-difluorophenyl)propane-1-sulfonamide;
N-(2,4-difluoro-3-(6-(2-fluoropyridin-3-yl)quinazolin-4-ylamino)phenyl)-3-fluoropropane-1-sulfonamide;
N-(3-(6-(2-(2-(dimethylamino)ethoxy)pyridin-4-yl)quinazolin-4-ylamino)-2,4-difluorophenyl)propane-1-sulfonamide;
N-(2,4-difluoro-3-(6-(5-fluoropyridin-3-yl)quinazolin-4-ylamino)phenyl)propane-1-sulfonamide;
N-(3-(6-(1H-benzo[d]imidazol-1-yl)quinazolin-4-ylamino)-2,4-difluorophenyl)propane-1-sulfonamide;
N-(2,4-difluoro-3-(6-(2-fluoropyridin-3-yl)quinazoline-4-carbonyl)phenyl)propane-1-sulfonamide;
N-(3-(6-ethynylquinazolin-4-ylamino)-2,4-difluorophenyl)propane-1-sulfonamide;
N-(3-(6-(2-aminopyrimidin-5-yl)quinazolin-4-ylamino)-2,4-difluorophenyl)propane-1-sulfonamide;
N-(3-(6-(2-(dimethylamino)pyrimidin-5-yl)quinazolin-4-ylamino)-2,4-difluorophenyl)propane-1-sulfonamide;

N-(3-(6-(1H-1,2,3-triazol-4-yl)quinazolin-4-ylamino)-2,4-difluorophenyl)propane-1-sulfonamide;

N-(2,4-difluoro-3-((6-(2-fluoropyridin-3-yl)quinazolin-4-yl)(methyl)amino)phenyl)-N-methylpropane-1-sulfonamide;

N-(3-(6-(6-(dimethylamino)pyridin-3-yl)quinazolin-4-ylamino)-2,4-difluorophenyl)propane-1-sulfonamide;

N-(2,4-difluoro-3-(6-(2-fluoropyridin-3-yl)quinazolin-4-ylamino)phenyl)propanesultam;

N-(2,4-difluoro-3-(5-fluoro-6-(2-fluoropyridin-3-yl)quinazolin-4-ylamino)phenyl)propane-1-sulfonamide;

N-(3-(6-(2-chloropyridin-3-yl)quinazolin-4-ylamino)-2,4-difluorophenyl)propane-1-sulfonamide;

N-(2,4-difluoro-3-(6-(6-methoxy-5-nitropyridin-3-yl)quinazolin-4-ylamino)phenyl)propane-1-sulfonamide;

N-(3-(6-(3-aminophenyl)quinazolin-4-yl amino)-2,4-difluorophenyl)propane-1-sulfonamide;

N-(3-(6-(5-amino-6-methoxypyridin-3-yl)quinazolin-4-ylamino)-2,4-difluorophenyl)propane-1-sulfonamide;

N-(3-(6-(6-aminopyridin-2-yl)quinazolin-4-ylamino)-2,4-difluorophenyl)propane-1-sulfonamide;

N-(2,4-difluoro-3-(6-(6-(trifluoromethyl)pyridin-2-yl)quinazolin-4-ylamino)phenyl)propane-1-sulfonamide;

N-(3-(6-(6-cyanopyridin-2-yl)quinazolin-4-ylamino)-2,4-difluorophenyl)propane-1-sulfonamide;

N-(3-(6-(2-cyanopyridin-3-yl)quinazolin-4-ylamino)-2,4-difluorophenyl)propane-1-sulfonamide;

N-(2,4-difluoro-3-(6-(5-(trifluoromethyl)pyridin-3-yl)quinazolin-4-ylamino)phenyl)propane-1-sulfonamide;

N-(2,4-difluoro-3-(6-(4-fluoropyridin-3-yl)quinazolin-4-ylamino)phenyl)propane-1-sulfonamide; or N-(3-(6-(6-amino-5-methylpyridin-3-yl)quinazolin-4-ylamino)-2,4-difluorophenyl)propane-1-sulfonamide.

\* \* \* \* \*